(12) United States Patent
Floeder et al.

(10) Patent No.: US 7,187,995 B2
(45) Date of Patent: Mar. 6, 2007

(54) MAXIMIZATION OF YIELD FOR WEB-BASED ARTICLES

(75) Inventors: Steven P. Floeder, Shoreview, MN (US); Brandon T. Berg, West Lakeland, MN (US); Carl J. Skeps, Lakeville, MN (US); James A. Masterman, Lake Elmo, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 1 day.

(21) Appl. No.: 11/025,242

(22) Filed: Dec. 29, 2004

(65) Prior Publication Data

US 2005/0141760 A1    Jun. 30, 2005

Related U.S. Application Data

(60) Provisional application No. 60/533,595, filed on Dec. 31, 2003, provisional application No. 60/533,596, filed on Dec. 31, 2003.

(51) Int. Cl.
*G06F 19/00* (2006.01)

(52) U.S. Cl. ............... 700/122; 700/110; 700/143; 382/141

(58) Field of Classification Search ......... 700/110, 700/122, 143; 382/141
See application file for complete search history.

(56) References Cited

U.S. PATENT DOCUMENTS

| | | | |
|---|---|---|---|
| 3,759,620 A | 9/1973 | Cushing et al. |
| 4,173,441 A | 11/1979 | Wolf |
| 4,211,132 A | 7/1980 | Nichols, III et al. |
| 4,330,356 A | 5/1982 | Grollimund et al. |
| 4,567,064 A | 1/1986 | Wöste |
| 4,629,312 A | 12/1986 | Pearce et al. |
| 4,700,627 A | 10/1987 | Hagler |
| 4,746,020 A | 5/1988 | Schenk |
| 4,752,897 A | 6/1988 | Zoller et al. |
| 4,776,023 A | 10/1988 | Hamada et al. |
| 4,828,156 A | 5/1989 | Whiteley et al. |
| 4,877,323 A | 10/1989 | Stillwagon |
| 4,905,159 A | 2/1990 | Loriot |
| 4,927,180 A | 5/1990 | Trundle et al. |
| 4,951,223 A | 8/1990 | Wales et al. |

(Continued)

FOREIGN PATENT DOCUMENTS

EP    0 898 163 A1    2/1999

(Continued)

OTHER PUBLICATIONS

Pending U.S. Appl. No. 10/669,197; Carl J. Skeps et al; entitled "Apparatus and Method for Automated Web Inspection", filed Sep. 24, 2003.

(Continued)

*Primary Examiner*—Michael D. Masinick
(74) *Attorney, Agent, or Firm*—Brian E. Szymanski; Steven A. Bern

(57) ABSTRACT

Techniques are described for inspecting a web and controlling subsequent conversion of the web into one or more products. A system, for example, comprises an imaging device, an analysis computer and a conversion control system. The imaging device images the web to provide digital information. The analysis computer processes the digital information to identify regions on the web containing anomalies. The conversion control system subsequently analyzes the digital information to determine which anomalies represent actual defects for a plurality of different products. The conversion control system determines a value for at least one product selection parameter for each of the products, and selects one of the products for conversion of the web based on the respective determined value. Exemplary product selection parameters include web utilization, unit product produced, estimated revenue or profit, process time, machine capacity and demand for the different products.

31 Claims, 17 Drawing Sheets

U.S. PATENT DOCUMENTS

| | | |
|---|---|---|
| 4,972,326 A | 11/1990 | Jung et al. |
| 5,062,331 A | 11/1991 | Michal et al. |
| 5,305,392 A | 4/1994 | Longest, Jr. et al. |
| 5,365,596 A | 11/1994 | Dante et al. |
| 5,403,722 A | 4/1995 | Floeder et al. |
| 5,415,123 A | 5/1995 | Ryder |
| 5,434,629 A | 7/1995 | Pearson et al. |
| 5,440,648 A | 8/1995 | Roberts et al. |
| 5,544,256 A | 8/1996 | Brecher et al. |
| 5,710,420 A | 1/1998 | Martin et al. |
| 5,760,414 A | 6/1998 | Taylor |
| 5,774,177 A | 6/1998 | Lane |
| 5,873,392 A | 2/1999 | Meyer et al. |
| 5,949,550 A | 9/1999 | Arndt et al. |
| 6,014,209 A | 1/2000 | Bishop |
| 6,031,931 A | 2/2000 | Chiu et al. |
| 6,092,059 A | 7/2000 | Straforini et al. |
| 6,100,989 A | 8/2000 | Leuenberger |
| 6,252,237 B1 | 6/2001 | Ramthun et al. |
| 6,259,109 B1 | 7/2001 | Dalmia et al. |
| 6,266,436 B1 | 7/2001 | Bett et al. |
| 6,266,437 B1 | 7/2001 | Eichel et al. |
| 6,272,437 B1 | 8/2001 | Woods et al. |
| 6,295,129 B1 | 9/2001 | Björk |
| 6,314,379 B1 | 11/2001 | Hu et al. |
| 6,330,350 B1 | 12/2001 | Ahn et al. |
| 6,404,910 B1 | 6/2002 | Ungpiyakul et al. |
| 6,407,373 B1 | 6/2002 | Dotan |
| 6,479,228 B2 | 11/2002 | Turner et al. |
| 6,484,306 B1 | 11/2002 | Bokor et al. |
| 6,496,596 B1 | 12/2002 | Zika et al. |
| 6,661,507 B2 | 12/2003 | Yoda et al. |
| 6,778,694 B1 | 8/2004 | Alexandre |
| 6,804,381 B2 | 10/2004 | Pang et al. |
| 6,845,278 B2 | 1/2005 | Popp et al. |
| 2002/0030704 A1 | 3/2002 | Komgold et al. |
| 2002/0039436 A1 | 4/2002 | Alumot et al. |
| 2002/0080347 A1 | 6/2002 | Yoda et al. |
| 2002/0110269 A1 | 8/2002 | Floeder et al. |

FOREIGN PATENT DOCUMENTS

| | | |
|---|---|---|
| EP | 0 681 183 A2 | 11/1999 |
| EP | 1 022 906 | 7/2000 |
| EP | 1 348 946 A1 | 10/2003 |
| JP | 62 093637 | 4/1987 |
| JP | 11 248641 | 9/1999 |
| JP | 2000 009447 | 1/2000 |
| JP | 2001 261191 | 9/2001 |
| JP | 2001261191 A * | 9/2001 |
| JP | 2002 243648 | 8/2002 |
| WO | WO 98/44336 | 10/1998 |
| WO | WO 99/10833 | 3/1999 |
| WO | WO 00/07031 | 2/2000 |
| WO | WO 01/02840 | 1/2001 |
| WO | WO 01/53811 A1 | 7/2001 |
| WO | WO 02/21105 | 3/2002 |
| WO | WO 02/065106 A1 | 8/2002 |
| WO | WO 02/065107 A2 | 8/2002 |

OTHER PUBLICATIONS

"A PC-Based Real Time Defect Imaging System for High Speed Web Inspection", by J.W. Roberts, S.D. Rose, G. Jullien, L. Nichols, G.Moroscher, P.T.Jenkins, S.G.Chamberlain, R. Mantha, and D.J. Litwiller, DALSA Inc., pp. 7-29-7-41.

"Real-Time Computer Vision on PC-Cluster and Its Application to Real-Time Motion Capture", by Daisaku Arita, Satoshi Yonemoto, and Rin-ichiro Taniguchi, Kyushu University, Japan, 2000, pp. 205-206.

Technical Paper "The Application of a Flexible Machine Vision Architecture to the Inspection of Continuous Process Materials", by Brad Harkavy, from VISION '89 Conference, Chicago, Illinois, MS89-165, attended on Apr. 24-27, 1989.

"Flexible Circuits, Roll-to-Roll AOI" by Brian Tithecott, PC FAB, pp. 26-32.

"A New Design Environment for Defect Detection Web Inspection Systems", by S. Hossain Hajimowlana, Roberto Muscedere, Graham A. Jullien, James W. Roberts, DALSA Inc.; SPIE vol. 3205, 1997, pp. 125-136.

"Parsytec HTS-2 Defect Detection and Classification Through Software vs. Dedicated Hardware", by Reinhard Rinn, Scott A. Thompson, Dr. Ralph Foehr, Friedrich Luecking, and John Torre; SPIE vol. 3645; Jan. 1999, pp. 110-121.

Wenyuan Xu et al., "Industrial Web Inspection for Manufacturing Process Understanding and Control", Proceedings of the SPIE—The International Society for Optical Engineering SPIE-INT., Soc. Opt. Eng. USA, vol. 3652, Jan. 1, 1999, pp. 10-20, XP002307220, ISSN: 0277-786X, Figure 1.

* cited by examiner

MAXIMIZATION OF YIELD FOR WEB-BASED ARTICLES

This application claims the benefit of U.S. Provisional Application No. 60/533,595, entitled "METHOD FOR THE OPTIMIZATION OF YIELDS ON WEB BASED ARTICLES," filed Dec. 31, 2003, and U.S. Provisional Application No. 60/533,596, entitled "METHOD FOR CONTROLLING INVENTORY OF WEB BASED ARTICLES," filed Dec. 31, 2003, the entire contents of each of which are incorporated herein by reference.

TECHNICAL FIELD

The present invention relates to automated inspection of systems, and more particularly, to optical inspection of webs.

BACKGROUND

Inspection systems for the analysis of moving web materials have proven critical to modern manufacturing operations. Industries as varied as metal fabrication; paper, nonwovens, and films rely on these inspection systems for both product certification and online process monitoring. One major difficulty in the industry is related to the extremely high data processing rates required to keep up with current manufacturing processes. With webs of commercially viable width and web speeds that are typically used and pixel sizes that are typically needed, data acquisition speeds of tens or even hundreds of megabytes per second are required of the inspection systems. It is a continual challenge to process images and perform accurate defect detection at these data rates.

The art has responded to this dilemma by limiting the image processing to very simple algorithms, by limiting the scope and complexity of the detection algorithms, and by using custom inspection system architectures incorporating custom electronic hardware or dedicated preprocessors, each working on part of the data stream. While such systems are capable of achieving the data rates required for the inspection of moving webs, is very difficult to adapt the system for a new production process and web materials. Also, processing algorithms are limited to the capabilities of dedicated processing modules. Finally, as the image processing algorithms become more complex, the hardware required to implement the required processing quickly becomes unmanageable.

The manufacturing industry has recognized the importance of being able to produce product "just-in-time" with obvious advantages in reduced inventory. However, achieving this goal often has manufacturers working to develop systems and devices that allow a rapid changeover between various products. The rapid changeover between products is inconsistent with the specialized signal processing hardware the art of optical inspection of moving webs now requires.

Another dilemma occurs in situations when a given product can be later used for multiple applications, with each of the multiple applications requiring different quality levels. The difficulty is that during the time of manufacture, it is not known which quality level will be required. Therefore, the current art attempts to grade quality level after defect detection by using various defect classification techniques based on spatial features of the extracted defects. While this is sometimes adequate when gross differences exist between defect levels for different quality requirements, it is not adequate for more demanding situations in which more subtle differences between defects require different image processing and defect extraction algorithms. Thus, if one waits until after defect extraction for classification, information is lost and the classification is impossible.

SUMMARY OF THE INVENTION

The invention is directed to techniques for the automated inspection of moving webs. An inspection system, for example, acquires anomaly information for a web using an optical acquisition device, and performs a preliminary examination with a first, typically less sophisticated algorithm. Image information about the regions of the web containing anomalies is stored for subsequent processing, accepting the likelihood that although some of the anomalies will be defective, many could be "false positives," i.e., anomalies that are not defective. In fact, some anomaly areas may be ultimately classified as defective if the web is used in a particular product application, but not defective if the web is used in another.

The original anomaly information can be reconsidered and fully analyzed at a convenient time, even after the inspected web has been wound onto a roll and is unavailable. As a result, the speed of the moving web during the inspection can be much greater than is possible when the entire surface of the web is subjected to a sophisticated analysis.

Moreover, conversion decisions can be made offline, and can be based on many factors. A conversion control system subsequently reconsiders the original image information, and subjects the image information to at least one of a variety of more sophisticated image processing and defect extraction algorithms to effectively separate actual defects from anomalies. The conversion control system utilizes the defect information to control the manner in which a web is ultimately converted to the products based on one or more product selection parameters.

Specifically, the conversion control system applies the image processing and defect extraction algorithms to generate defect information for a number of potential web-based products, i.e., products into which the web could be converted. The conversion control system then identifies which product best achieves the selected parameters, such as a maximum utilization of the web. Other examples of product selection parameters that may be used to influence the conversion selection process include unit product produced, estimated revenue or profit from the produced product, process time required to convert the web, current machine capacity for each process line, current demand for the different products or other parameters.

In one embodiment, a method comprises imaging a sequential portion of a web to provide digital information, and processing the digital information with at least one initial algorithm to identify regions on the web containing anomalies. The method further comprises analyzing at least a portion of the digital information with a plurality of subsequent algorithms to determine which anomalies represent actual defects in the web for a plurality of different products, determining a value of at least one product selection parameter for each of the products, selecting one of the products based on the determined value for each of the products, and converting the web into the selected product.

In another embodiment, a system comprises an imaging device, an analysis computer, and a conversion control system. The imaging device images a sequential portion of a web to provide digital information. The analysis computer processes the digital information with an initial algorithm to identify regions on the web containing anomalies. The conversion control system analyzes at least a portion of the digital information with at least one subsequent algorithm to determine which anomalies represent actual defects in the web for a plurality of different products. Further, the conversion control system determines a value for at least one product selection parameter for each of the products, and selects one of the products for conversion of the web based on the respective determined value for each of the products.

In another embodiment, a conversion control system comprises a database storing data defining a set of rules, and an interface to receive anomaly information from an analysis machine, wherein the anomaly information identify regions of a web containing anomalies. The conversion control system further comprises a conversion control engine that applies the rules to the anomaly information to determine a value for at least one product selection parameter for each of a plurality of products. The conversion control engine selects one of the products for conversion of the web based on the determined values In another embodiment, a computer-readable medium comprises instructions that cause a processor to store data defining a set of rules, and receive anomaly information from an analysis machine located within a manufacturing plane, wherein the anomaly information identify regions of a web containing anomalies. The instructions further cause the processor to apply the rules to the anomaly information to determine a value for at least one product selection parameter for each of a plurality of products; and select one of the products for conversion of the web based on the determined values.

The invention may offer one or more advantages. For example, the capture and storage of anomaly information for subsequent analysis allow application-specific defect detection methods to be applied, which may provide enhanced defect detection capability. Further, the techniques allow conversion decisions for a given roll or web to be based on one or more parameters, such as web or product yield, revenue, profit, current process line capacity, current product demand or other parameters.

The details of one or more embodiments of the invention are set forth in the accompanying drawings and the description below. Other features, objects, and advantages of the invention will be apparent from the description and drawings, and from the claims.

DEFINITIONS

For purposes of the present invention, the following terms used in this application are defined as follows:

"web" means a sheet of material having a fixed dimension in one direction and either a predetermined or indeterminate length in the orthogonal direction;

"sequential" means that an image is formed by a succession of single lines, or areas of the web that optically map to a single row of sensor elements (pixels);

"pixel" means a picture element represented by one or more digital values;

"blob" means a connected set of pixels in a binary image;

"defect" means an undesirable occurrence in a product;

"anomaly" or "anomalies" mean a deviation from normal product that may or may not be a defect, depending on its characteristics and severity.

"gray scale" means pixels having a multitude of possible values, e.g. 256 digital values;

"binarization" is an operation for transforming a pixel into a binary value;

"filter" is a mathematical transformation of an input image to a desired output image, filters are typically used to enhance contrast of a desired property within an image;

"application-specific" means defining requirements, e.g., grade levels, based on the intended use for the web;

"yield" represents a utilization of a web expressed in percentage of material, unit number of products or some other manner;

"fiducial marks" means reference points or notations used to define specific, physical locations on the web;

"products" are the individual sheets (also referred to as component) produced from a web, e.g., a rectangular sheet of film for a cell phone display or a television screen; and "conversion" the process of physically cutting a web into products.

DETAILED DESCRIPTION

Figure 1:
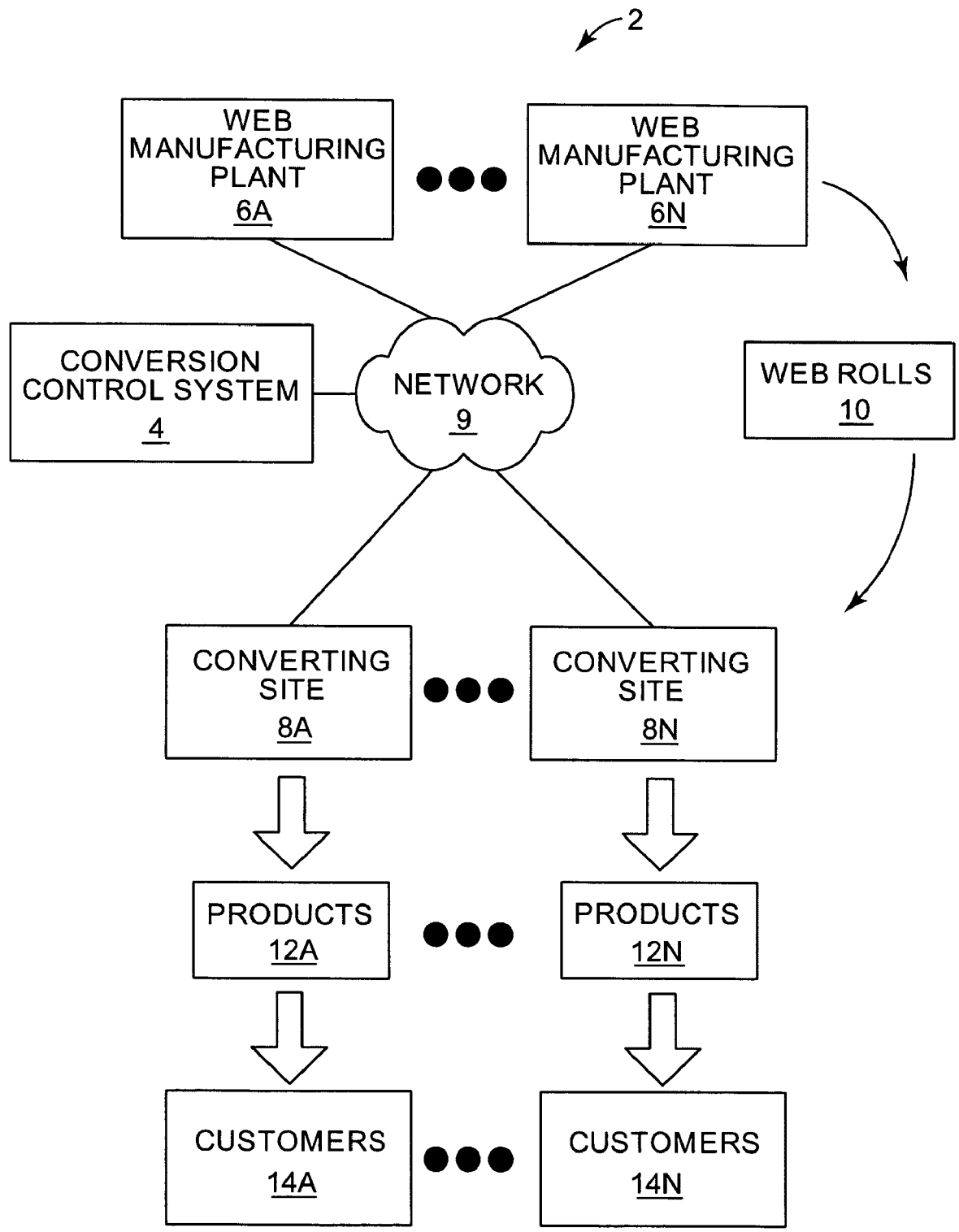
FIG. 1 is a block diagram illustrating a global network environment in which a conversion control system controls conversion of web material in accordance with the invention.

FIG. 1 is a block diagram illustrating a global network environment 2 in which conversion control system 4 controls conversion of web material. More specifically, web manufacturing plants 6A–6N represent manufacturing sites that produce and ship web material in the form of web rolls 10. Web manufacturing plants 6A–6N may be geographically distributed.

The manufactured web material may include any sheet-like material having a fixed dimension in one direction and either a predetermined or indeterminate length in the orthogonal direction. Examples of web materials include, but are not limited to, metals, paper, wovens, non-wovens, glass, polymeric films, flexible circuits or combinations thereof. Metals may include such materials as steel or aluminum. Wovens generally include various fabrics. Non-wovens include materials, such as paper, filter media, or insulating material. Films include, for example, clear and opaque polymeric films including laminates and coated films.

For many applications, the web materials of web rolls 10 may have an applied coating, which generally are applied to an exposed surface of the base web material. Examples of coatings include adhesives, optical density coatings, low adhesion backside coatings, metalized coatings, optically active coatings, electrically conductive or nonconductive coatings, or combinations thereof. The coating may be applied to at least a portion of the web material or may fully cover a surface of the base web material. Further, the web materials may be patterned or unpatterned.

Web rolls 10 are shipped to converting sites 8A–8N, which may be geographically distributed within different countries. Converting sites 8A–8N ("converting sites 8") convert each web roll 10 into one or more products. Specifically, each of converting sites 8 includes one or more process lines that physically cut the web for a given web roll 10 into numerous individual sheets, individual parts, or numerous web rolls, referred to as products 12A–12N. As one example, converting site 8A may convert web rolls 10 of film into individual sheets for end use applications. Similarly, other forms of web materials may be converted into products 12 of different shapes and sizes depending upon the intended application by customers 14A–14N. Each of converting sites 8 may be capable of receiving different types of web rolls 10, and each converting site may produce different products 12 depending on the location of the converting site and the particular needs of customers 14.

As described in detail herein, each of web manufacturing plants 6 includes one or more inspection systems (not shown in FIG. 1) that acquire anomaly information for the produced webs. The inspection systems of web manufacturing plants 6 perform preliminary examination of the webs using a first, typically less sophisticated algorithm to identify manufacturing anomalies, accepting the likelihood that although some of the anomalies may prove defective, many could be "false positives," i.e., anomalies that are not defective. In fact, products 12 have different grade levels, also referred to as quality levels, and have different tolerances for manufacturing anomalies. As a result, some of the anomaly areas may be ultimately classified as defective if the corresponding web roll 10 is converted to a particular product 12, but not defective if the web roll is converted to a different product.

Web manufacturing plants 6 communicate image information about the regions of the web containing anomalies to conversion control system 4 via network 9 for subsequent processing. Conversion control system 4 applies one or more defect detection algorithms that may be application-specific, i.e., specific to products 12. Based on the analysis, conversion control system 4 determines, in an automated or semi-automated manner, which of products 12 would allow a particular web roll 10 to achieve a maximum yield (i.e., utilization) of the web. Based on the determination, conversion control system 4 generates a conversion plan for each web roll 10, i.e., defined instructions for processing the web roll, and communicates the conversion plan via network 9 to the appropriate converting site 8 for use in converting the web into the selected product.

Conversion control system 4 may consider other product selection parameters, either in addition to or independent from yield, when generating conversion plans for each of web rolls 10. For example, conversion control system 4 may consider the number of units that 10 would be produced by each of web rolls 10 for the different products 12. Other example product selection parameters that conversion control system 4 may consider when generating a conversion plan include an estimated amount of revenue or profit that would be produced by the web roll for each potential product 12, a process time that would be required to convert the web for each of the different products, a current machine capacity for each process line within converting sites 8, current levels of demand for each of products 12 and other parameters.

In certain embodiments, conversion control system 4 may make such determinations for individual converting sites 8. In other words, conversion control system 4 may identify the web rolls destined for each converting site 8, and generate conversion plans based on the products 12 associated with the individual converting sites. For example, conversion control system 4 may identify the web rolls destined for converting site 8A, and generate conversion plans to maximize yield for the web rolls based on the products 12A produced by converting site 8A.

Alternatively, conversion control system 4 may generate the conversion plans for web rolls 10 prior to their shipment to converting sites 8. Consequently, conversion control system 4 may consider all of the potential available products 12 when generating corresponding conversion plans for web rolls 10. In this manner, conversion control system 4 may consider all of the potentially available products 12 in order to, for example, maximize the yield of each web roll 10. In this configuration, conversion control system 4 generates conversion plans and outputs instructions identifying the specific converting sites 8 to which each of web rolls 10 should be shipped.

In some embodiments, conversion control system 4 considers other parameters when selecting the respective converting sites 8 for web rolls 10. Such parameters include, but are not limited to, current inventory levels of products 12 at each of converting sites 8, recent orders received from customers 14, shipment time and cost associated with each of converting sites 8, methods of available shipment and other parameters.

In this manner, conversion control system 4 applies application-specific defect detection algorithms to the anomaly information received from web manufacturing plants 6, and ultimately directs the conversion of web rolls 10 into products 12 based on one or more parameters. As illustrated below, these factors may be user selectable, and may be applied independently or collectively using a weighting function or other technique.

Figure 2:
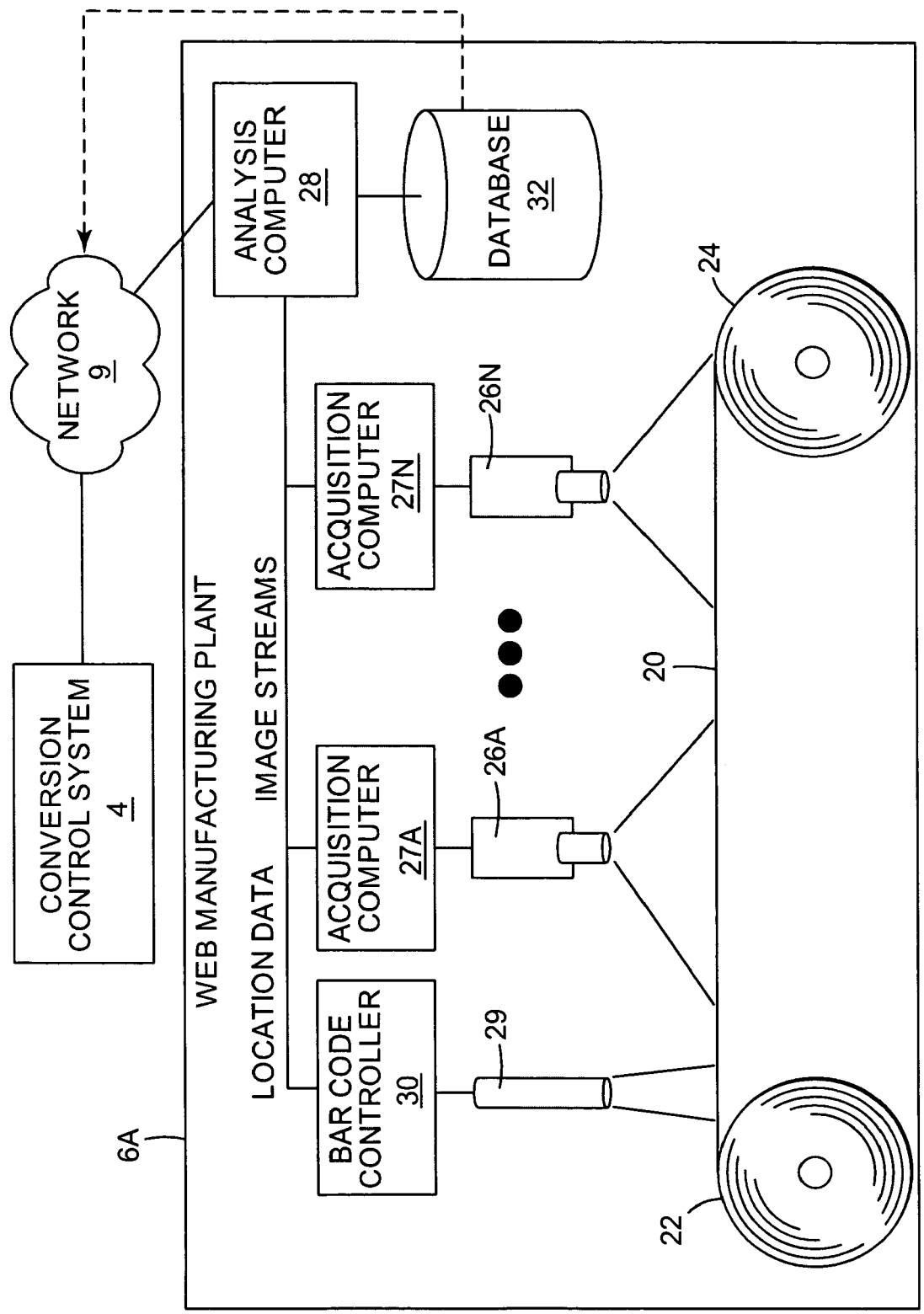
FIG. 2 is a block diagram illustrating an exemplary embodiment of a web manufacturing plant.

FIG. 2 is a block diagram illustrating an exemplary embodiment of web manufacturing plant 6A of FIG. 1. In the exemplary embodiment, a segment of a continuously moving web 20 is positioned between two support rolls 22, 24.

Image acquisition devices 26A–26N are positioned in close proximity to the continuously moving web 20. Image acquisition devices 26 scan sequential portions of the continuously moving web 20 to obtain image data. Acquisition computers 27 collect image data from image acquisition devices 26, and transmit the image data to analysis computer 28 for preliminary analysis.

Image acquisition devices 26 may be conventional imaging devices that are capable of reading a sequential portion of the moving web 20 and providing output in the form of a digital data stream. As shown in FIG. 2, imaging devices 26 may be cameras that directly provide a digital data stream or an analog camera with an additional analog to digital converter. Other sensors, such as, for example, laser scanners may be utilized as the imaging acquisition device. A sequential portion of the web indicates that the data is acquired by a succession of single lines. Single lines comprise an area of the continuously moving web that optically maps to a single row of sensor elements or pixels. Examples of devices suitable for acquiring the image include linescan cameras such as Model#LD21 from Perkin Elmer (Sunnyvale, Calif.), Piranha Models from Dalsa (Waterloo, Ontario, Canada), or Model#TH78H15 from Thompson-CSF (Totawa, N.J.). Additional examples include laser scanners from Surface Inspection Systems GmbH (Munich, Germany) in conjunction with an analog to digital converter.

The image may be optionally acquired through the utilization of optic assemblies that assist in the procurement of the image. The assemblies may be either part of a camera, or may be separate from the camera. Optic assemblies utilize reflected light, transmitted light, or transflected light during the imaging process. Reflected light, for example, is often suitable for the detection of defects caused by web surface deformations, such as surface scratches.

Barcode controller 30 controls barcode reader 29 to input roll and position information from web 20. Barcode controller 30 communicates the roll and position information to analysis computer 28.

Analysis computer 28 processes image streams from acquisition computers 27. Analysis computer 28 processes the digital information with one or more initial algorithms to generate anomaly information that identifies any regions of web 20 containing anomalies that may ultimately qualify as defects. For each identified anomaly, analysis computer 28 extracts from the image data an anomaly image that contains pixel data encompassing the anomaly and possibly a surrounding portion of web 20.

Analysis computer 28 stores roll information, position information and anomaly information within database 32. Database 32 may be implemented in any of a number of different forms including a data storage file or one or more database management systems (DBMS) executing on one or more database servers. The database management systems may be, for example, a relational (RDBMS), hierarchical (HDBMS), multidimensional (MDBMS), object oriented (ODBMS or OODBMS) or object relational (ORDBMS) database management system. As one example, database 32 is implemented as a relational database provided by SQL Server™ from Microsoft Corporation.

Analysis computer 28 communicates the roll information as well as anomaly information and respective sub-images to conversion control system 4 for subsequent, offline, detailed analysis. For example, the information may be communicated by way of a database synchronization between analysis computer 28 and conversion control system 4.

Figure 3:
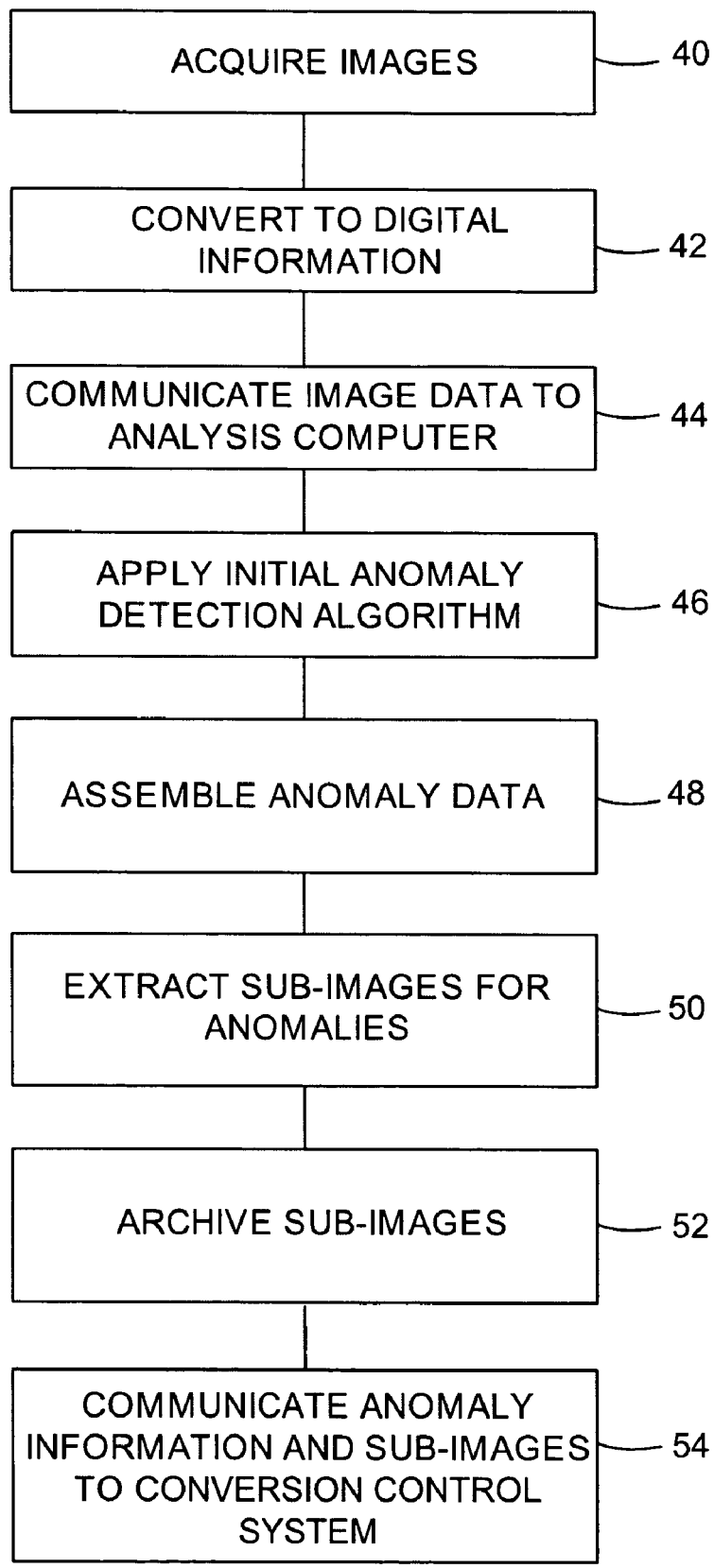
FIG. 3 is a flowchart illustrating exemplary operation of the web manufacturing plant.

FIG. 3 is a flowchart illustrating exemplary operation of web manufacturing plant 6A. Initially, image acquisition devices 26 and acquisition computers 27 acquire image data from moving web 20 (40). The image data may be formed digitally, e.g., by way of a digital video camera, or may be converted to digital information (42). In either case, acquisition computers 27 output streams of digital image information to analysis computer 28 (44).

Analysis computer 28 applies an initial anomaly detection algorithm to identify regions of the web containing anomalies (46). In some convenient embodiments, the initial anomaly detection algorithm is very fast so as to be capable of being performed in real time by general purpose computing equipment even if a line speed of moving web 20 is great. As a result, some of the identified regions containing anomalies may include "false positives." Even though there may be many false positives, the initial algorithm is preferably designed such that "escapes," i.e., true defects not detected as anomalies, rarely, if ever occur.

Upon applying the initial anomaly detection algorithm, analysis computer 28 assembles anomaly data about the identified regions and stores the anomaly data within database 32 (48). The data typically includes a start position of the anomaly within the web and an encompassing pixel area of each identified region. During this process, analysis computer 28 extracts a portion of the image data for each identified region containing an anomaly (50). Specifically, only a fraction of the original digital image information needs to be extracted for further, more sophisticated analysis by conversion control system 4. The identified regions typically contain information, for example, at least an order of magnitude less than the digital information, as indicated by size in any convenient measure such as file size in bytes. In some applications, the present invention has demonstrated actual data reduction in an order of magnitude of between 3 and 12.

The extracted anomaly images may be stored in a database 32 or a file server (not shown) (52) and subsequently communicated to conversion control system 4 along with the anomaly and roll information (54). Alternatively, the roll information, anomaly information and anomaly images may be transferred directly for processing by conversion control system 4.

Figure 4:
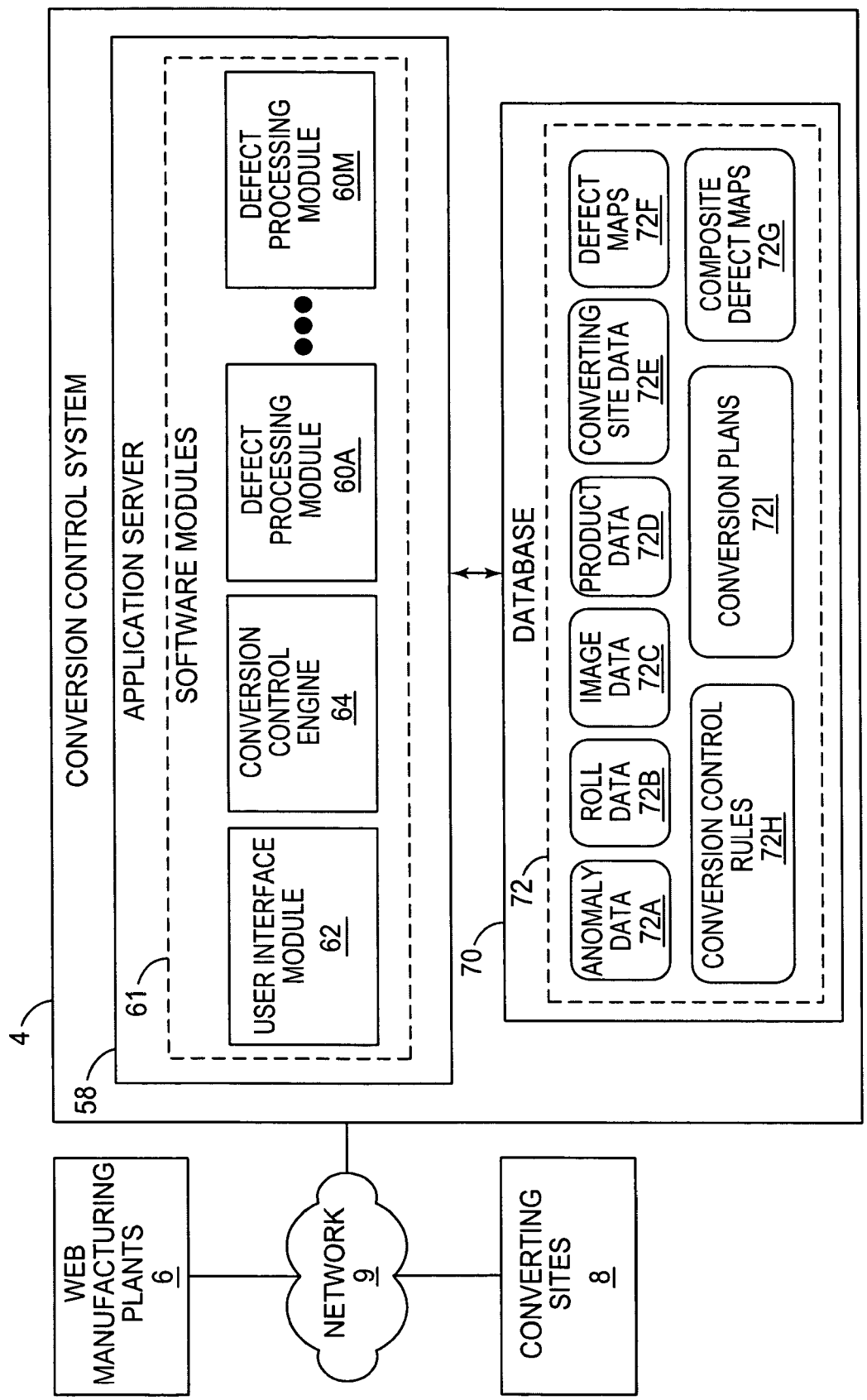
FIG. 4 is a block diagram illustrating an example embodiment of a conversion control system.

FIG. 4 is a block diagram illustrating an example embodiment of conversion control system 4 in further detail. In the example embodiment, application server 58 provides an operating environment for software modules 61. Software modules include a plurality of defect processing modules 60A–60M, a user interface module 62 and a conversion control engine 64.

Software modules 61 interact with database 70 to access data 72, which may include anomaly data 72A, roll data 72B, image data 72C, product data 72D, converting site data 72E, defect maps 72F, composite defect maps 72G, conversion control rules 72H, and conversion plans 72I.

Database 70 may be implemented in any of a number of different forms including a data storage file or one or more database management systems (DBMS) executing on one or more database servers. As one example, database 32 is implemented as a relational database provided by SQL Server™ from Microsoft Corporation.

Anomaly data 72A, roll data 72B, and image data 72C represent the roll information, anomaly information and respective anomaly images received from web manufacturing plants 6 (FIG. 1). Product data 72D represents data associated with products 12 (FIG. 1). More specifically, product data 72D defines each type of product 12 producible by each converting site 8. For each product 12, product data 72D specifies one or more defect processing modules 60 that are required to determine whether a given web roll 10 satisfies the quality requirements for the particular product. In other words, product data 72D specifies one or more defect processing modules 60 that are to be used to analyze anomaly data 72A and image data 72C for each product 12.

In addition, product data 72D stores other information related to products 12 that may be utilized by conversion control system 4 when selecting converting sites 8 and generating conversions plans for web rolls 10. For example, product data 72D may further include data specifying an estimated revenue per unit for each of products 12. Product data 72D may also include data specifying an estimated income per unit for each of products 12, an estimated conversion time to convert a web roll to each product, a current level of industry demand for each of product or other data that may be useful in selecting conversion plans.

Converting site data 72E represents data associated with converting sites 8. For example, converting site data 72E may stores site location, number of process lines and a current available capacity of each process line for each of converting sites 8. Converting site data 72E may store other data, including but not limited to, data specifying a current level of inventory for each product 12 at each converting site 8, shipments costs associated with shipping a web roll to each converting site, shipment options available for each converting site, current order information from customers 14 received by each converting site, data specifying new or preferred customers for each converting site, and other data that may be useful in selecting conversion plans.

As described in further detail below, defect processing modules 60 output defect maps 72F that specify which anomalies are considered actual defects for the different products 12. In other words, each defect map 72F corresponds to a particular web roll 10 and a specific product 12. Each defect map 72F specifies the particular defect locations of a particular web roll 10 based on the product-specific requirements of the corresponding product 12.

Conversion control engine 64 analyzes defect maps 72F in accordance with conversions control rules 72H to select the ultimate conversion used for each of the web rolls 10. For example, conversion control engine 64 may analyze defect maps 72F to determine which of products 12 would allow a particular web roll 10 to achieve a maximum yield (i.e., utilization) of the web. Conversion control rules 72H specify one or more parameters for consideration by conversion control engine 64 when processing defect maps 72F, such as usage of web material, the number of units that would be produced by each of web rolls 10 for the different products 12, an estimated amount of revenue or profit that would be produced by the web roll for each potential product 12, a process time that would be required to convert the web for each of the different products, a current machine capacity for each process line within converting sites 10, current levels of demand for each of products 12 and other parameters.

During this process, conversion control engine 64 may determine that a particular web roll 10 may be best utilized (e.g., may achieve maximum yield) if converted into multiple products 12. In other words, conversion control engine 64 may determine that a first portion of the web may be best utilized when converted to a first product, and a second portion for a different product. In this case, conversion control engine 64 generates a "composite" defect map 72G that specifies the defect locations within each portion of the web based on the corresponding product to which the portion is to be converted. Conversion control engine 64 may create the composite defect maps by splicing portions of two or more defect maps 72F to form a complete, composite defect map for the entire web.

Upon selecting a particular product or set of products for a given web roll 10, conversion control engine 64 generates a respective conversion plan 72I. Each conversion plan 72I provides precise instructions for processing the respective web roll. More specifically, each conversion plan 72I defines configurations for processing lanes to physically slice the web into individual product sheets. Conversion control system 4 outputs shipment instructions directing the shipment of each web roll 10 to a respective destination converting site 8. Further, conversion control system 4 communicates conversion plans via network 9 to the appropriate converting sites 8 for use in converting the web rolls into the selected products.

User interface module 62 provides an interface by which a user can configure the parameters used by conversion control engine 64. For example, as illustrated below, user interface module 62 allows the user to direct conversion control engine 64 to consider one or more of a maximum web utilization, number of units produced, estimated revenue, estimated profit, machine capacity, current levels of demand and/or other parameters.

Figure 5:
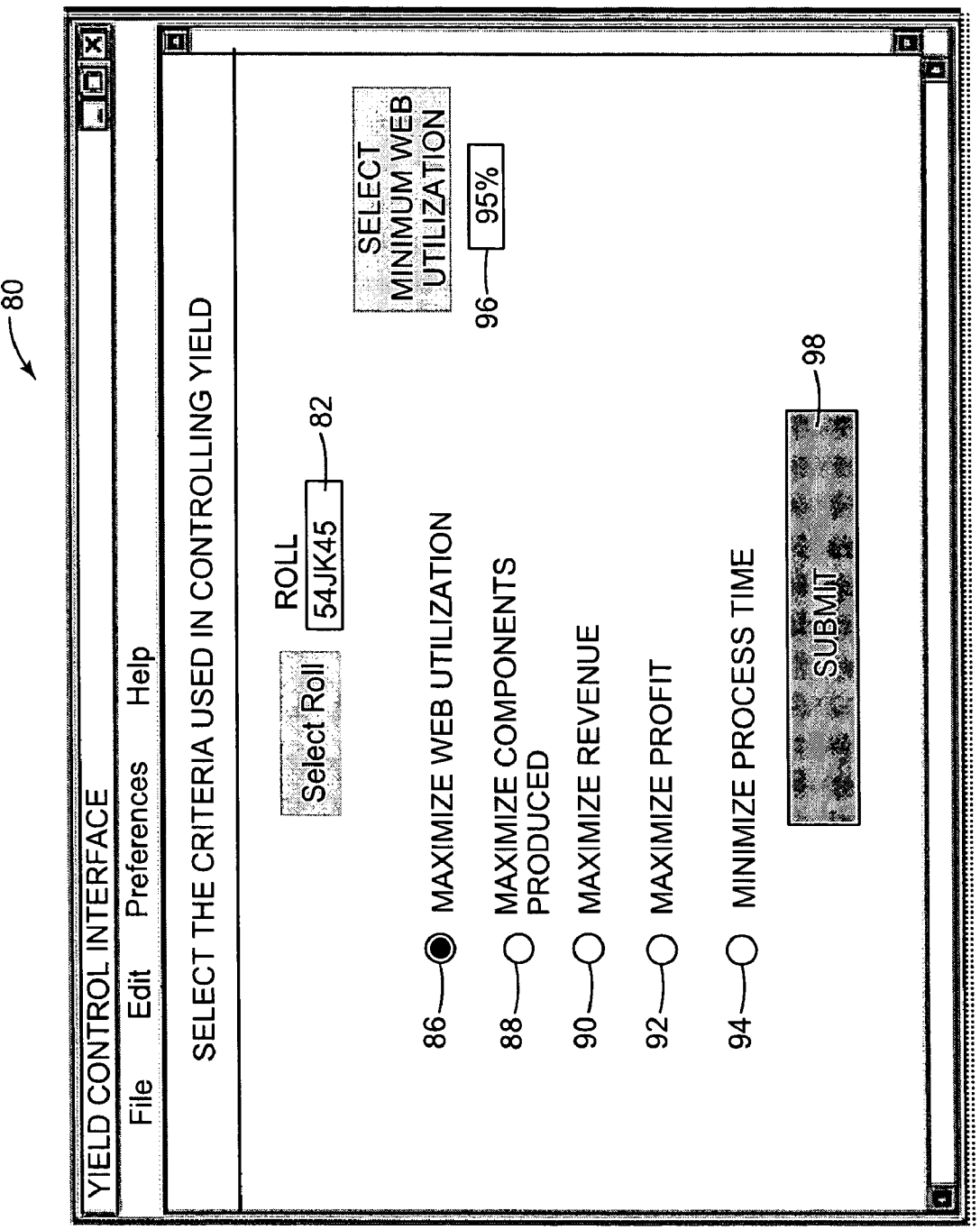
FIG. 5 is an example user interface presented by a user interface module with which a user interacts to configure the conversion control system.

FIG. 5 is an example user interface 80 presented by user interface module 62 with which a user interacts to configure conversion control engine 64. Exemplary interface 80 includes input mechanism 82 by which the user enters a unique identifier for a web roll. Other mechanisms for selecting a roll may be used, such as a drop-down menu, search function, selectable list of recently manufactured rolls or the like.

In addition, user interface 80 provides a plurality of input mechanisms 86–94 by which the user can select one or more product selection parameters for consideration by conversion control engine 64 when generating a recommended conversion plan. In this example, user interface 80 includes a first input selection mechanism 86 to direct conversion control engine 64 to select a conversion plan that seeks to optimize the web utilization for the selected web roll. Input mechanism 88 directs conversion control engine 64 to maximize the number of components produced from selected web roll. Similarly, input mechanisms 90, 92 direct conversion control engine 64 to maximize the revenue and profit generated from selected web roll, respectfully. Input mechanism 94 directs conversion control engine 64 to select a conversion plan that minimizes the process time for selected web roll. Upon selection of one or more parameters, the user selects SUBMIT button 98, which directs conversion control system 4 to process the selected web roll with defect processing modules 60, followed by analysis and conversion plan selection by conversion control engine 64.

In this manner, user interface 80 provides a simplistic illustration of how a user may configure conversion control engine 64 based on one or more parameters. User interface 80 may require the user to select one and only one of the input mechanisms 86–94. In certain embodiments, user interface 80 includes an input mechanism 96 that allows the user to define a minimum web utilization. This may be advantageous in situations where the user selects a primary parameter, such as profit, to be maximized, but desires a baseline utilization to be met.

Figure 6:
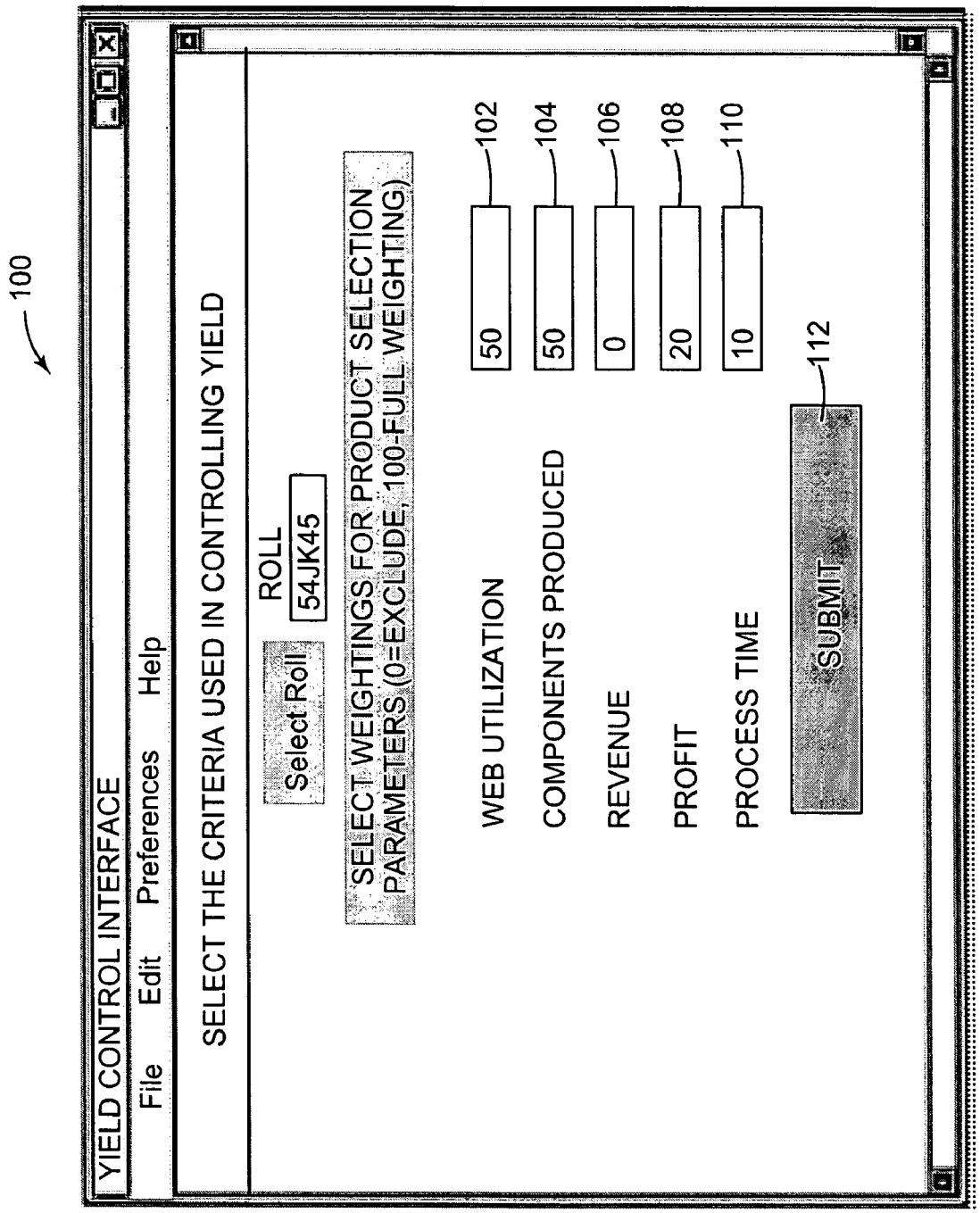
FIG. 6 provides another exemplary user interface presented by the user interface module.

FIG. 6 provides another exemplary user interface 100 presented by user interface module 62. In this embodiment, exemplary interface 100 includes input mechanisms 102–110 by which the user enters respective weighting functions for each parameter. Specifically, input mechanism 102 allows the user to enter a weighting function ranging from 0 to 100 for each parameter, where 0 directs conversion control engine 64 to exclude the parameter and 100 represents the highest possible weighting.

Defect processing modules 60 analyze the anomaly data for the selected web roll when the user selects SUBMIT button 112, followed by analysis and conversion plan selection by conversion control engine 64.

When selecting a conversion plan for a given web roll 10, conversion control engine 64 may analyze defect maps 72F for each potential product 12 for each of the parameters having non-zero weightings. In the example of FIG. 6, conversion control engine 64 analyzes the defect maps 72F and product data 72D to compute web utilization, number of components produced, profit generated and process time for each potential product. As described in further detail below, conversion control engine 64 may then normalize the computed results of each parameter for each product, and then compute weighted values from the normalized results. Finally, conversion control engine 64 selects a conversion plan as a function of (e.g., a sum) of the weighted values. Other technique may be utilized in which conversion control system 4 utilizes multiple parameters when selecting a conversion plan for a web roll 10.

Figure 7:
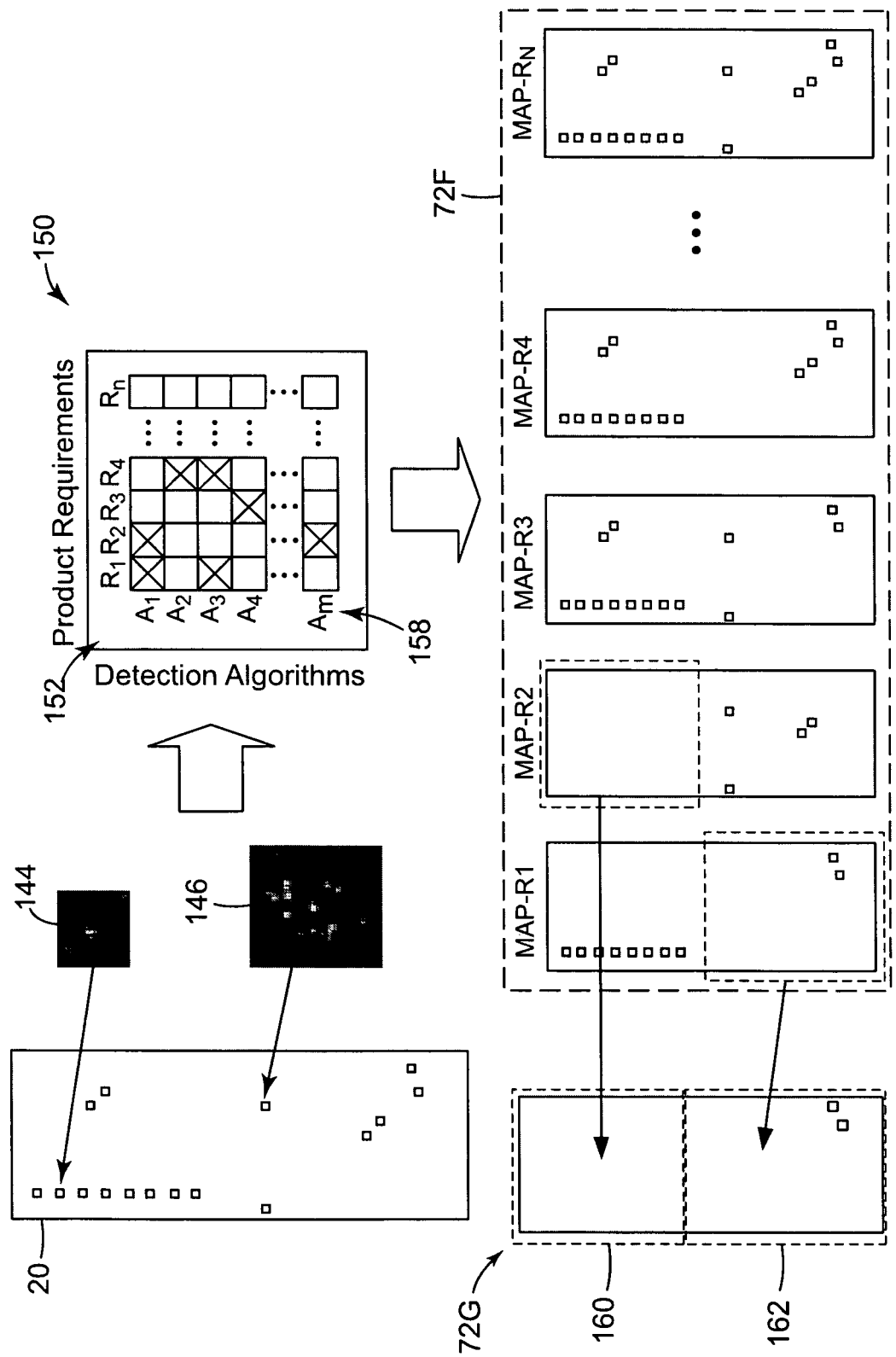
FIG. 7 is a flow diagram that illustrates exemplary processing of anomaly information by the conversion control system.

FIG. 7 is a flow diagram that illustrates the processing of anomaly information by conversion control system 4 in further detail. In particular, FIG. 7 illustrates the processing of anomaly data 72A and image data 72C by defect processing modules 60.

Conversion control system 4 receives the image and anomaly data, such as images 144, 146, that were extracted initially from a web 20 by an analysis computer 28 located at a web manufacturing plant 6 using a simple first detection algorithm.

As illustrated in FIG. 7, defect processing modules 60 apply "M" different algorithms (designated $A_1$–$A_m$ 158 in FIG. 7) as needed for up to N different requirements 150 for products 12. Cross-reference table 152 of FIG. 7 is used to illustrate the mapping between requirements 150 and defect processing modules 60. Specifically, cross-reference table 152 shows which defect processing modules 60 are utilized in determining whether each anomaly is a defect or a false positive for a given requirement 150.

In some embodiments, a larger number of rather simpler algorithms are conveniently used in parallel. In particular, it is often convenient that at least one of the subsequent defect processing modules 60 apply an algorithm that includes comparing each anomaly against a combination threshold-pixel size criterion. In actual practice with, for example, optical films, an anomaly having only a subtle difference in brightness value from a target is unacceptable if the area is large, and an anomaly having a great difference in brightness from a target value is unacceptable even if the area is very small.

In addition, the algorithms applied by defect processing modules 60 can incorporate very complex image processing and defect extraction including, but not limited to, neighborhood averaging, neighborhood ranking, contrast expansion, various monadic and dyadic image manipulations, digital filtering such as Laplacian filters, Sobel operators, high-pass filtering and low-pass filtering, texture analysis, fractal analysis, frequency processing such as Fourier transforms and wavelet transforms, convolutions, morphological processing, thresholding, connected component analyses, blob processing, blob classifications, or combinations thereof. Other algorithms may be applied based on the specific web and defect types to achieve a desired accuracy level of defect detection.

Each of the N product requirements 150 can be accomplished using selected combinations of individual defect processing algorithms 158. The algorithms may use very simple threshold and minimum blob processing or more complex algorithms such as spatial filters, morphological operations, frequency filters, wavelet processing, or any other known image processing algorithms. In this exemplary cross-reference table 152, product requirement $R_1$ uses a combination of algorithms $A_2$, $A_4$, and $A_M$, each applied to every anomaly image to determine which anomalies are actual defects for $R_1$. In most convenient embodiments, a simple OR logic is employed, i.e. if any of $A_2$, $A_4$, and $A_M$ report the anomaly as an actual defect, that portion of web 20 does not satisfy product requirement $R_1$. For specialized applications, the logic through which the reports of the subsequent algorithms 158 are combined into a determination of whether a product requirement 150 is satisfied may be more complex than a simple OR logic. Similarly, product requirement $R_2$ uses $A_2$, $A_3$, and $A_4$, etc. Thus, the anomalies that are identified as defects for $R_2$ may be similar to or significantly different than defects for $R_1$.

After determining which anomalies are considered actual defects by using cross-reference table 152, conversion control engine 64 formulates defect maps 72F of actual defect locations corresponding to the various product requirements for the roll. In some situations, conversion control engine 64 may generate one or more composite defect maps 72G by splicing one or more portions of defect maps 72F. In this illustrated example, conversion control engine 64 generates a composite map 72G having a first portion 160 spliced from a defect map for a first product requirement (MAP-R1) and a second portion 162 from a defect map for a second product requirement (MAP-R2). In this manner, conversion control engine 64 may determine that a web may be best utilized if certain portions of the web are converted into different products. Once this has been done, it is often possible to discard the subimage information to minimize the needed storage media.

Further details of image processing and subsequent application of the anomaly detection algorithms applied by defect processing modules 60 are described by commonly assigned and co-pending U.S. patent application Ser. No. 10/669,197, entitled "APPARATUS AND METHOD FOR AUTOMATED WEB INSPECTION," having filed Apr. 24, 2003, the entire contents of which are incorporated herein by reference.

FIGS. 8–15 are flowcharts illustrating various exemplary embodiments in which conversion control engine 64 applies conversion rules 72H to generate conversion plans 72I based on one or more user-configurable parameters, such as usage of web material, number of units produced, revenue, profit, process time, machine capacity, product demand and other parameters.

Figure 8:
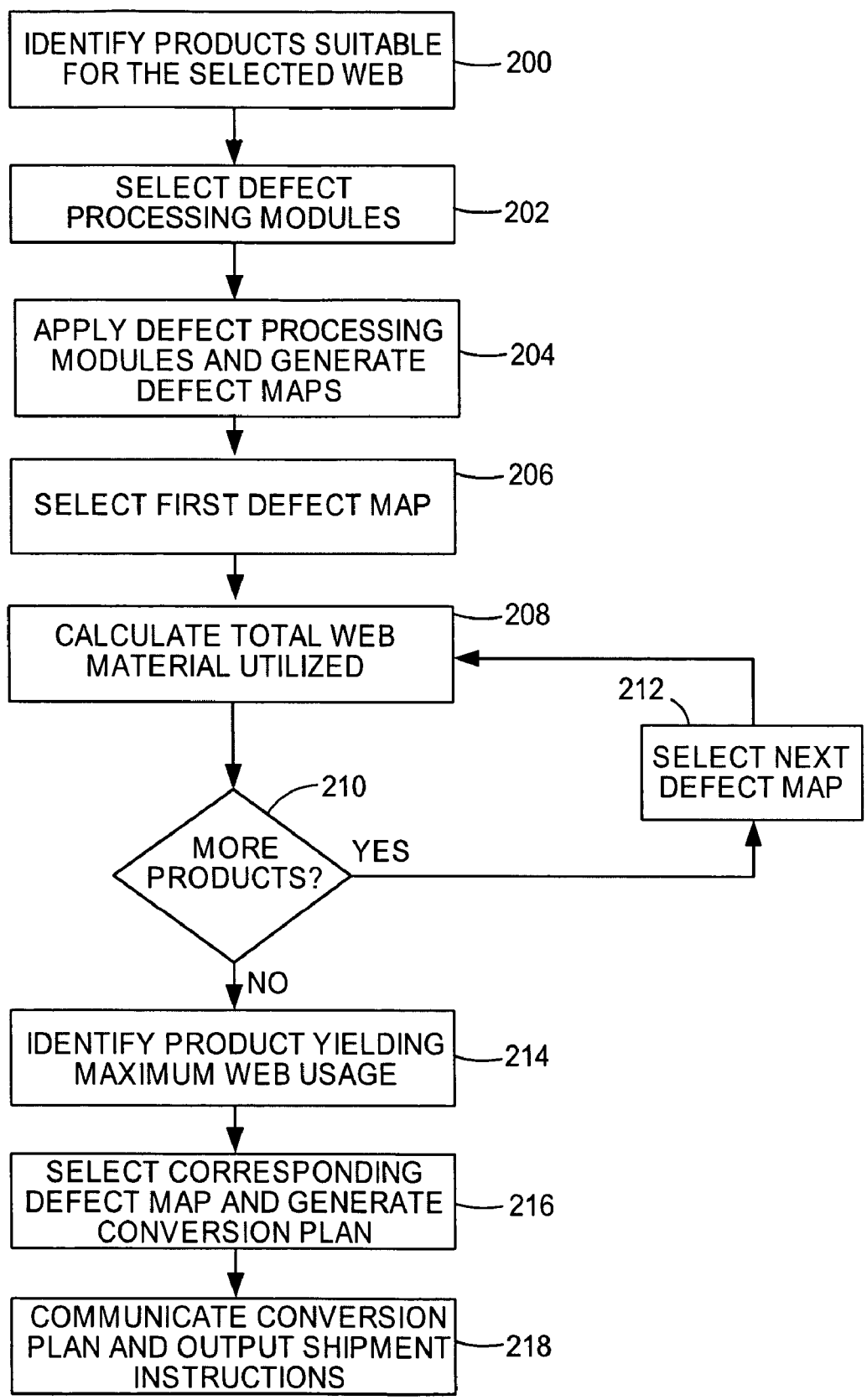
FIG. 8 is a flowchart illustrating one exemplary method in which a conversion control engine generates a conversion plan for a given web roll to maximize web utilization.

FIG. 8 is a flowchart illustrating one exemplary method in which conversion control engine 64 selects a conversion plan 72I for a given web roll 10 to maximize web utilization. Initially, conversion control engine 64 identifies a set of potential products 12 into which the web roll 10 may be converted (200). As described above, if the web roll has been or is currently being shipped to a particular converting site 8, conversion control engine 64 selects one or more of the products associated with the specific converting site for which the web roll is suitable. Alternatively, if the web roll being considered has not been shipped, conversion control system 4 may select all of products 12 for which the web roll is suitable.

Conversion control engine 64 accesses product data 72D of database 70 to identify the product requirements for the identified set of suitable products, and selects one or more of the defect processing modules 60 based on the identified requirements (202).

Next, conversion control engine 64 invokes the selected defect processing modules 60, which apply respective defect detection algorithms to anomaly data 72A and image data 72C received from a web manufacturing plant 6 to formulate defect information for each of the product requirements. Conversion control engine 64 generates defect maps 72F based on the defects identified by defect processing modules 60 (204).

In the example of FIG. 8, conversion control engine 64 selects a first one of the defect maps (206), and analyzes the map to calculate a yield for the web, either in percentage of material utilized, actual area utilized or some other convenient metric (208). Conversion control engine 64 repeats this process for each defect map (210, 212).

Conversion control engine 64 then selects the product that would result in the maximum yield for the web roll (214). Conversion control engine 64 identifies the defect map associated with the selected product, and generates a conversion plan 72I in accordance with the selected defect map (216).

Conversion control engine 64 may further communicate the conversion plan to the appropriate converting site 8, and output (e.g., display or print) shipment instructions for shipping the particular web roll 10 to the converting site (218).

Figure 9:
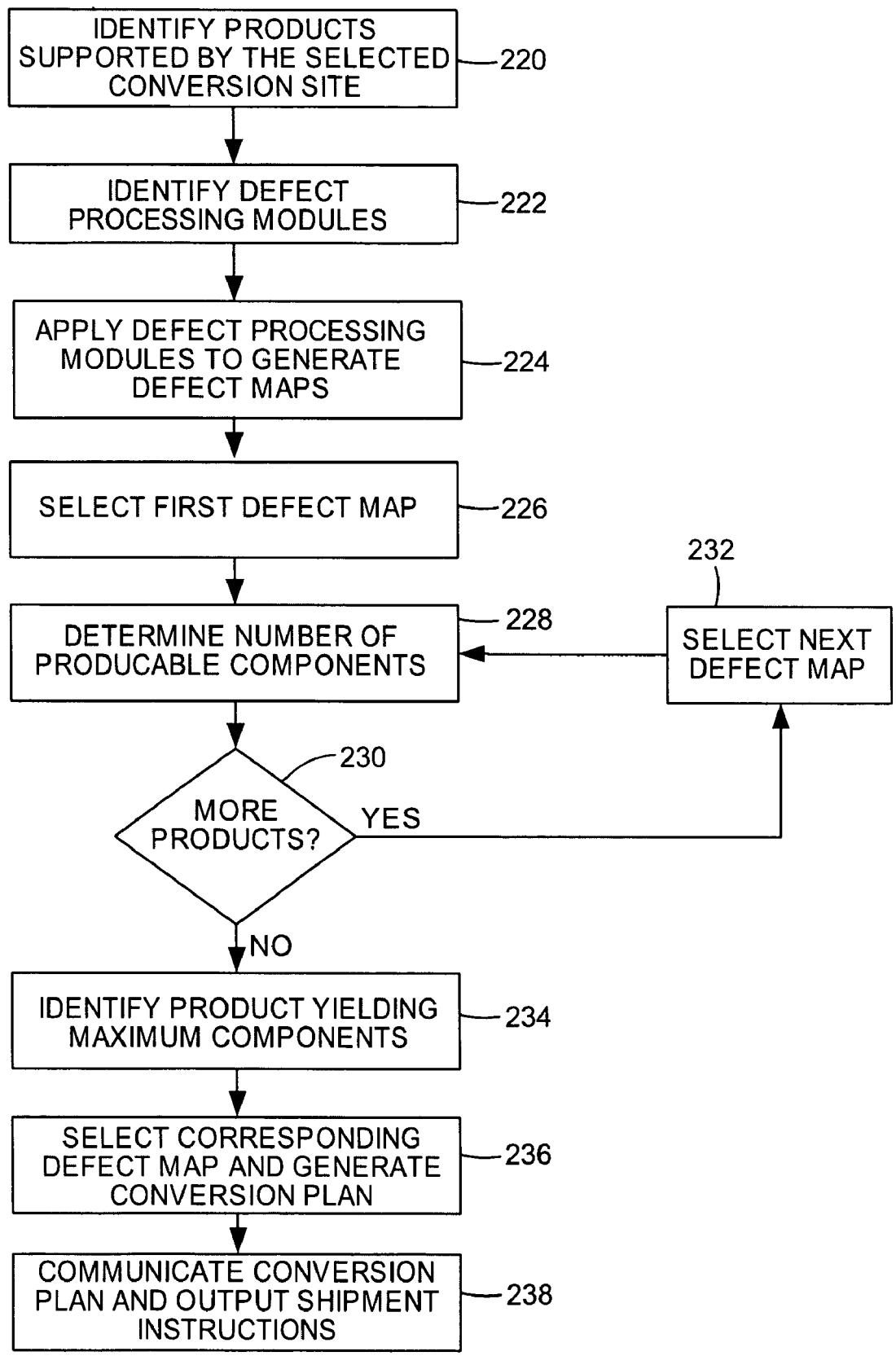
FIG. 9 is a flowchart illustrating an exemplary method in which the conversion control engine generates a conversion plan to maximize the number of components produced from the web roll.

FIG. 9 is a flowchart illustrating an exemplary method in which conversion control engine 64 generates a conversion plan 72I for a given web roll 10 to maximize the number of components produced from the web roll. As described above, conversion control engine 64 identifies a set of potential products 12 into which the web roll 10 may be converted, and selectively invokes one or more of the defect processing modules 60 to apply defect detection algorithms and generates defect maps 72F for the web roll (220–224).

In the example method of FIG. 9, conversion control engine 64 selects a first one of the defect maps (226), and analyzes the map to calculate a total number of components that could be produced for the respective product (228). Conversion control engine 64 repeats this process for each defect map (230, 232).

Conversion control engine 64 then selects the product that would result in the maximum number of components produced by the web roll (234). For example, based on the specific locations of the defects, few components may be realizable for a larger sized product (e.g., a film for a computer screen) versus a smaller sized product (e.g., a film for a mobile phone display).

Conversion control engine 64 generates a conversion plan 72I based on the selected product, communicates the conversion plan to the appropriate converting site 8, and outputs (e.g., display or print) shipment instructions for shipping the particular web roll 10 to the converting site (236–238).

Figure 10:
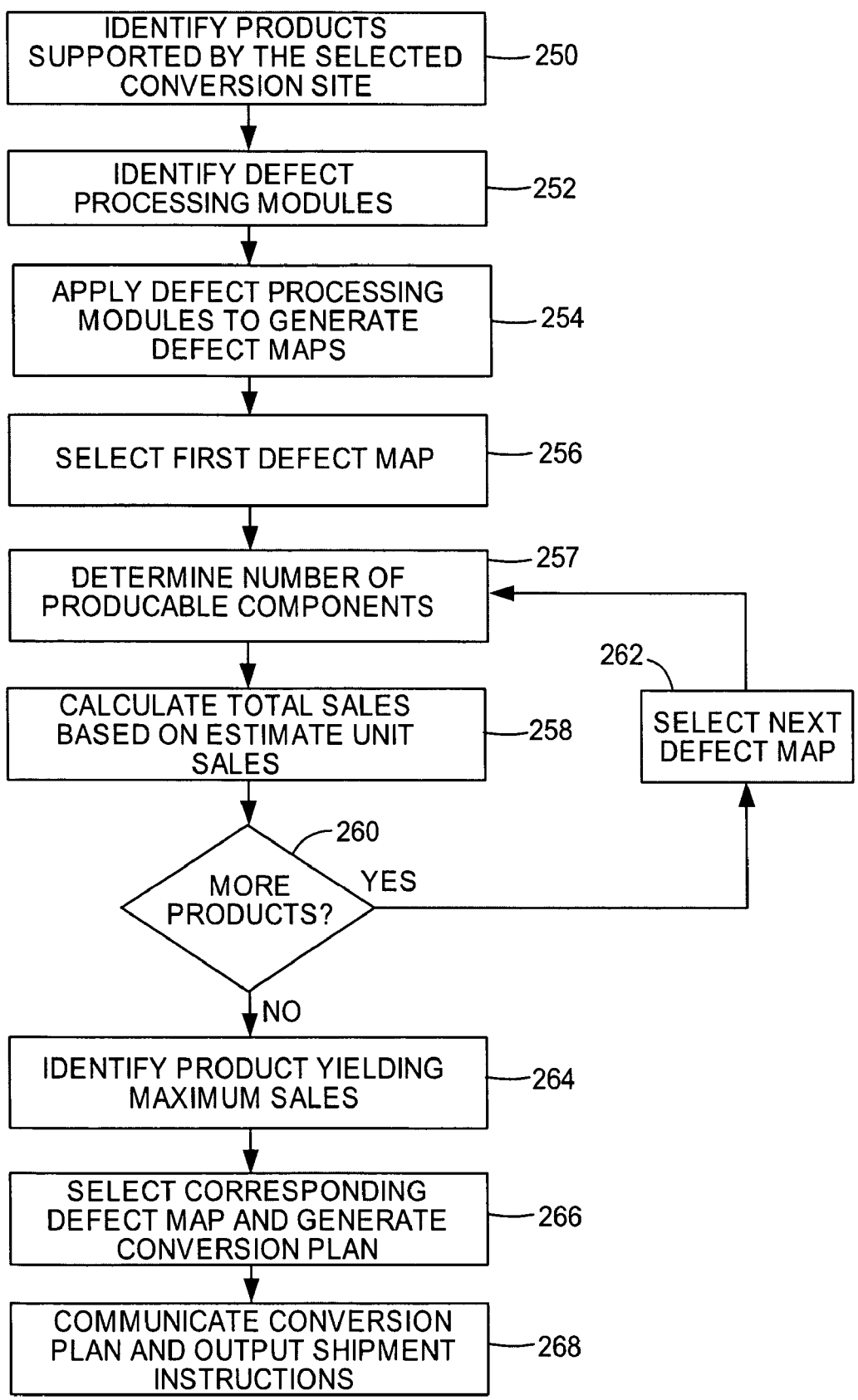
FIG. 10 is a flowchart illustrating an exemplary method in which the conversion control engine generates a conversion plan for a given web roll to maximize a total unit sales volume realized from the web roll.

FIG. 10 is a flowchart illustrating an exemplary method in which conversion control engine 64 generates a conversion plan 72I for a given web roll 10 to maximize a total unit sales volume realized from the web roll. As described above, conversion control engine 64 identifies a set of potential products 12 into which the web roll 10 may be converted, and selectively invokes one or more of the defect processing modules 60 to apply defect detection algorithms and generates defect maps 72F for the web roll (250–254).

Next, conversion control engine 64 selects a first one of the defect maps (256), and analyzes the map to calculate a total number of components that could be produced for the respective product (257). Next, conversion control engine 64 accesses product data 72D to retrieve an estimated sale price per unit for the particular product. Based on the estimated sale price, conversion control engine 64 calculates a total estimated sales (e.g., in dollars) that would be generated from the web roll if the web roll were converted into the product (258). Conversion control engine 64 repeats this process for each defect map (260, 262).

Conversion control engine 64 then selects the product that would result in the maximum amount of realized sales, i.e., revenue, for the web roll (264). For example, certain components may better capture a premium price than other components due to market factors. In this exemplary embodiment, conversion control engine 64 may select a product that does not achieve a maximum utilization of the web roll, but nevertheless is expected to generate higher sales relative to the other suitable products.

Conversion control engine 64 generates a conversion plan 72I based on the selected product, communicates the conversion plan to the appropriate converting site 8, and outputs (e.g., display or print) shipment instructions for shipping the particular web roll 10 to the converting site (266–268).

Figure 11:
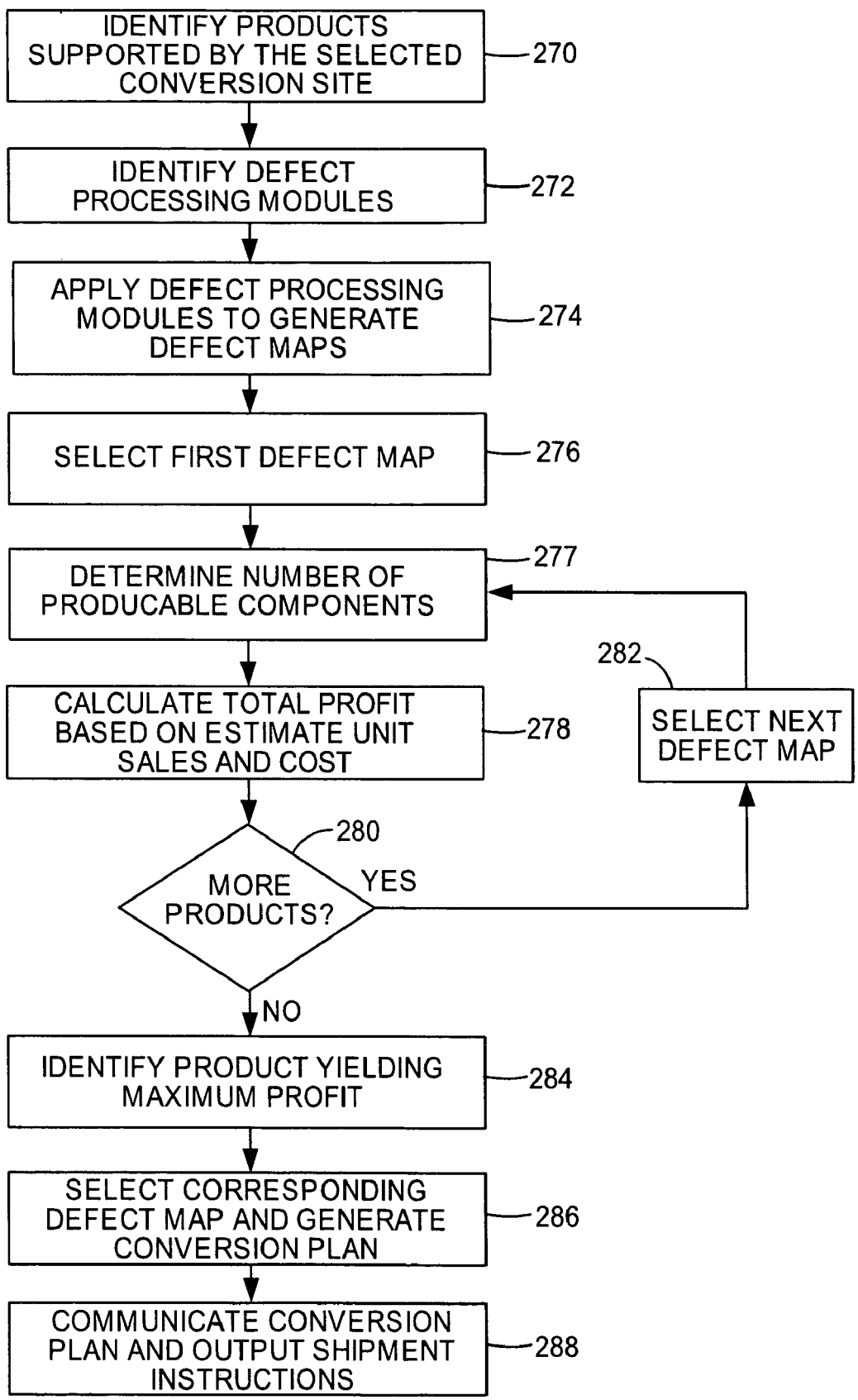
FIG. 11 is a flowchart illustrating an exemplary method in which the conversion control engine generates a conversion plan to maximize a total profit realized from the web roll.

FIG. 11 is a flowchart illustrating an exemplary method in which conversion control engine 64 generates a conversion plan 72I for a given web roll 10 to maximize a total profit realized from the web roll. As described above, conversion control engine 64 identifies a set of potential products 12 into which the web roll 10 may be converted, and selectively invokes one or more of the defect processing modules 60 to apply defect detection algorithms and generates defect maps 72F for the web roll (270–274).

Conversion control engine 64 then selects a first one of the defect maps (276), and analyzes the map to calculate a total number of components that could be produced for the respective product (277). Next, conversion control engine 64 accesses product data 72D to retrieve an estimated sales price and estimated cost per unit for the particular product. Based on the estimated sales price and cost, conversion control engine 64 calculates a total estimated profit realized from the web roll if the web roll were converted into the product (278). Conversion control engine 64 repeats this process for each defect map (280, 282).

Conversion control engine 64 then selects the product that would result in the maximum amount of profit realized for the web roll (284). Conversion control engine 64 generates a conversion plan 72I based on the selected product, communicates the conversion plan to the appropriate converting site 8, and outputs (e.g., display or print) shipment instructions for shipping the particular web roll 10 to the converting site (286–288).

Figure 12:
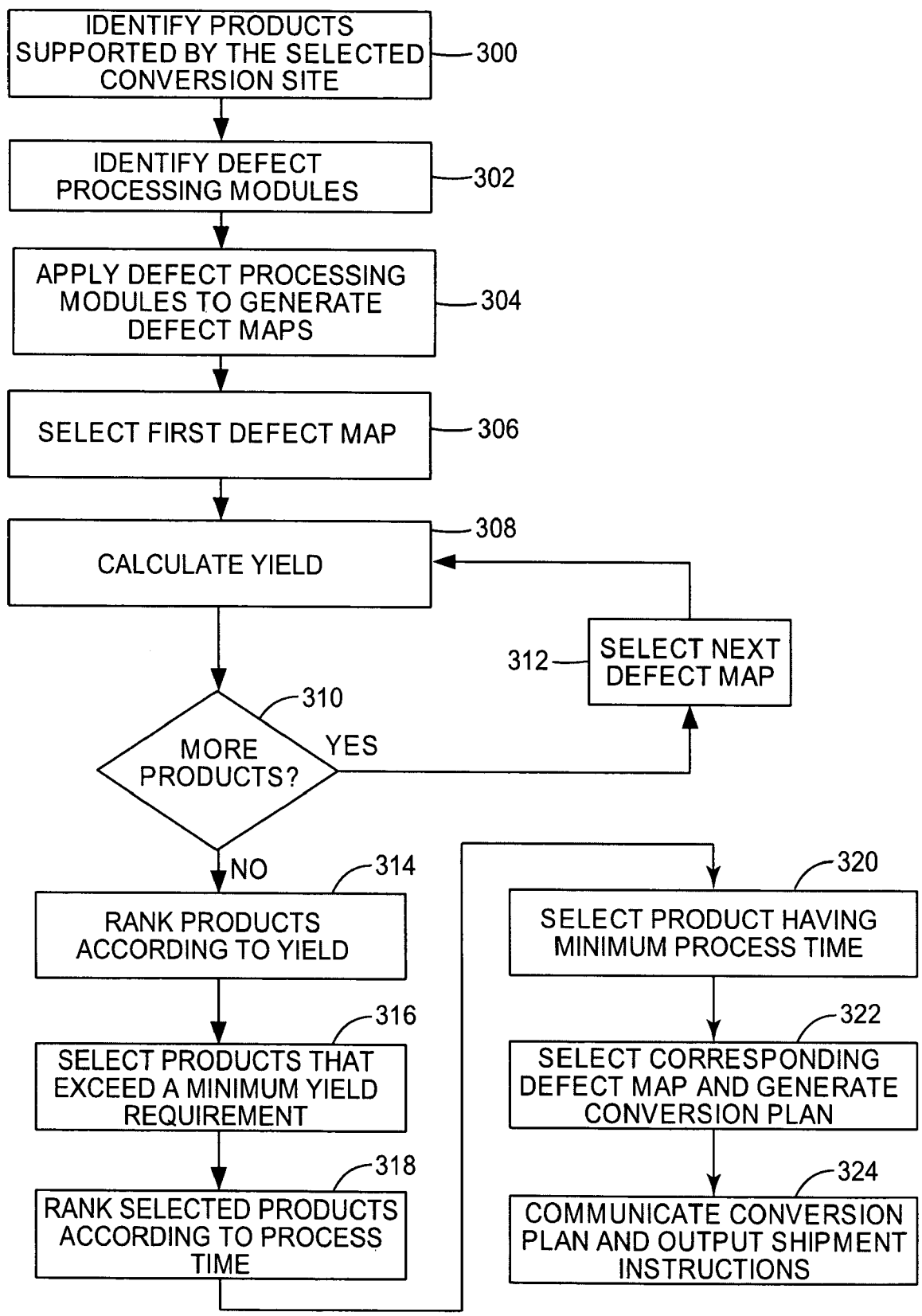
FIG. 12 is a flowchart illustrating an exemplary method in which the conversion control engine generates a conversion plan to minimize process time for a web roll yet achieve a defined minimum yield.

FIG. 12 is a flowchart illustrating an exemplary method in which conversion control engine 64 generates a conversion plan 72I for a given web roll 10 to minimize process time yet achieve a required minimum yield. As described above, conversion control engine 64 identifies a set of potential products 12 into which the web roll 10 may be converted, and selectively invokes one or more of the defect processing modules 60 to apply defect detection algorithms and generates defect maps 72F for the web roll (300–304).

Next, conversion control engine 64 selects a first one of the defect maps (306), and analyzes the map to calculate a yield that would be produced for the respective product, either as a percentage of material utilized, actual area utilized or some other convenient metric (308). Conversion control engine 64 repeats this process for each defect map (310, 312).

Conversion control engine 64 then ranks the products according to the estimated yield (314), and selects a subset of the products including only those products that would achieve a defined minimum yield (316). Next, conversion control engine 64 ranks the subset of products according to a process time, as specified in product data 72D (318). Conversion control engine 64 then selects the product from the subset of products that has the lowest estimated process time (320). Conversion control engine 64 generates a conversion plan 72I based on the selected product, communicates the conversion plan to the appropriate converting site 8, and outputs (e.g., display or print) shipment instructions for shipping the particular web roll 10 to the converting site (322–324). In this manner, conversion control engine 64 defines a conversion plan 72I for web roll 10 to achieve an acceptable yield level while minimizing conversion time (i.e., maximizing throughput) of the web at converting sites 8.

Figure 13:
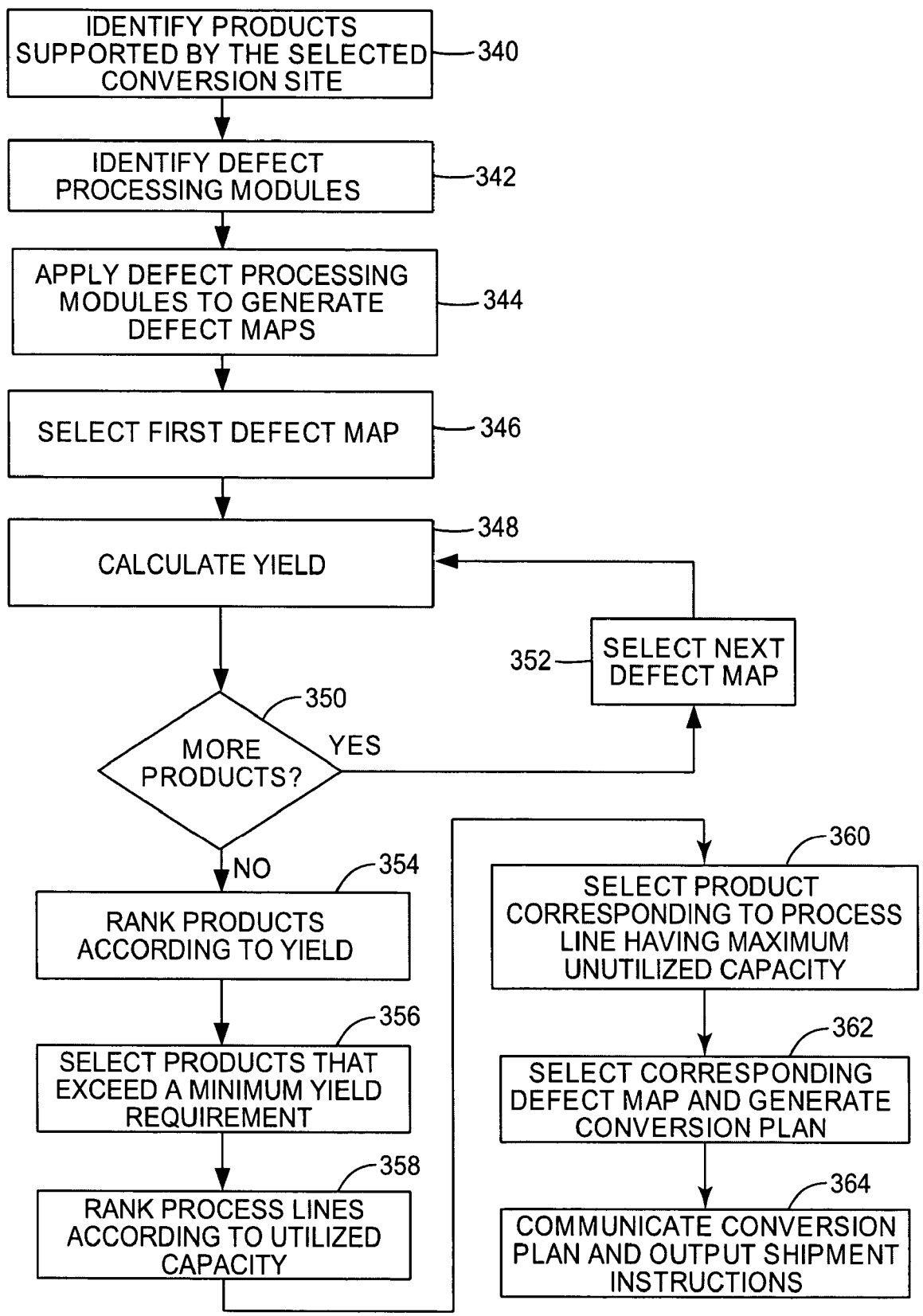
FIG. 13 is a flowchart illustrating an exemplary method in which the conversion control engine generates a conversion plan to maximize utilization of process lines at one or more converting sites, yet achieve a defined minimum yield for the web roll.

FIG. 13 is a flowchart illustrating an exemplary method in which conversion control engine 64 generates a conversion plan 72I for a given web roll 10 to maximize utilization of process lines at converting sites 8, yet achieve a required minimum yield for the web roll. As described above, conversion control engine 64 identifies a set of potential products 12 into which the web roll 10 may be converted, and selectively invokes one or more of the defect processing modules 60 to apply defect detection algorithms and generates defect maps 72F for the web roll (340–344).

Next, conversion control engine 64 selects a first one of the defect maps (346), and analyzes the map to calculate a yield that would be produced for the respective product, either as a percentage of material utilized, actual area utilized or some other convenient metric (348). Conversion control engine 64 repeats this process for each defect map (350, 352).

Conversion control engine 64 then ranks the products according to the estimated yield (354), and selects a subset of the products including only those products that would achieve a defined minimum yield (356). Next, conversion control engine 64 accesses converting site data 72E to determine a set of process lines of converting sites 8 suitable for converting the subset of products. Conversion control engine 64 ranks the identified process lines according to current unutilized capacity (358). Conversion control engine 64 then selects the product from the subset of products that corresponds to the process line having the highest unutilized capacity (360). Conversion control engine 64 generates a conversion plan 72I based on the selected product, communicates the conversion plan to the appropriate converting site 8, and outputs (e.g., display or print) shipment instructions for shipping the particular web roll 10 to the converting site (362–364). In this manner, conversion control engine 64 defines a conversion plan 72I for web roll 10 to achieve an acceptable yield level while maximizing the utilization of the process lines of converting sites 8.

Figure 14:
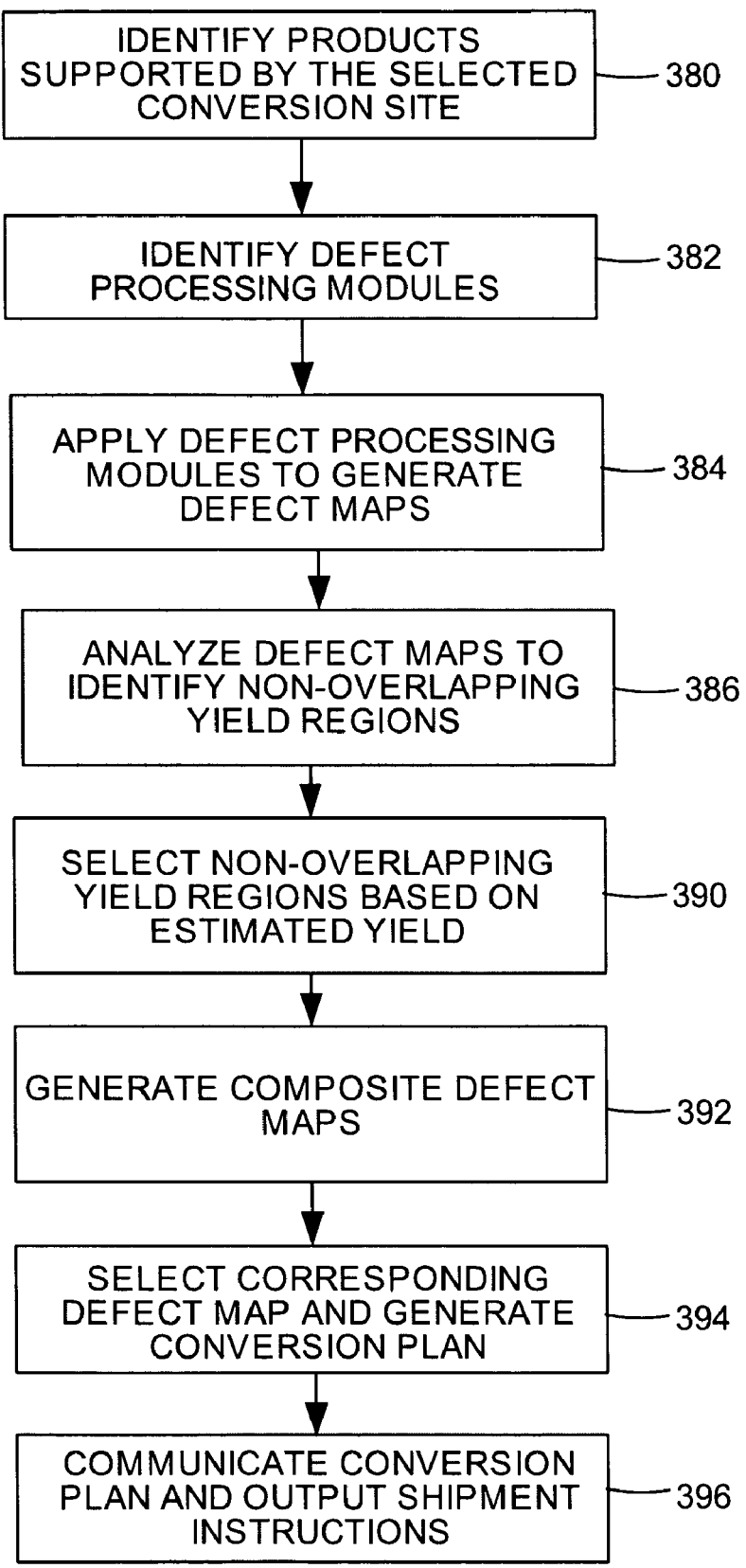
FIG. 14 is a flowchart illustrating an exemplary method in which the conversion control engine generates a conversion plan based on a composite defect map to convert the web roll into two or more products to maximize utilization of the web roll.

FIG. 14 is a flowchart illustrating an exemplary method in which conversion control engine 64 generates a conversion plan 72I for a given web roll 10 based on a composite defect map to convert the web roll into two or more products to maximize utilization of the web roll. As described above, conversion control engine 64 identifies a set of potential products 12 into which the web roll 10 may be converted, and selectively invokes one or more of the defect processing modules 60 to apply defect detection algorithms and generates defect maps 72F for the web roll (380–384).

Next, conversion control engine 64 analyzes the defect maps to define regions of the maps based on yield (386). For example, as illustrated in FIG. 7, based on the analysis, conversion control engine 64 may define a first region of one of the defect maps that would result in a relatively high yield for a first product, and a second non-overlapping region of a different product map that would result in a high yield for a second product.

Conversion control engine 64 ranks and selects the non-overlapping regions based on estimated yield (390), and generates a composite defect map 72G by splicing the non-overlapping regions to form the composite defect map (392). In this manner, conversion control engine 64 may determine that a web may be best utilized if certain portions of the web are converted into different products.

Conversion control engine 64 generates a conversion plan 72I based on the composite defect map, communicates the conversion plan to the appropriate converting site 8, and outputs (e.g., display or print) shipment instructions for shipping the particular web roll 10 to the converting site (362–364). In this manner, conversion control engine 64 defines a conversion plan 72I for web roll 10 to convert the web roll into two or more products to maximize utilization of the web roll.

Figure 15:
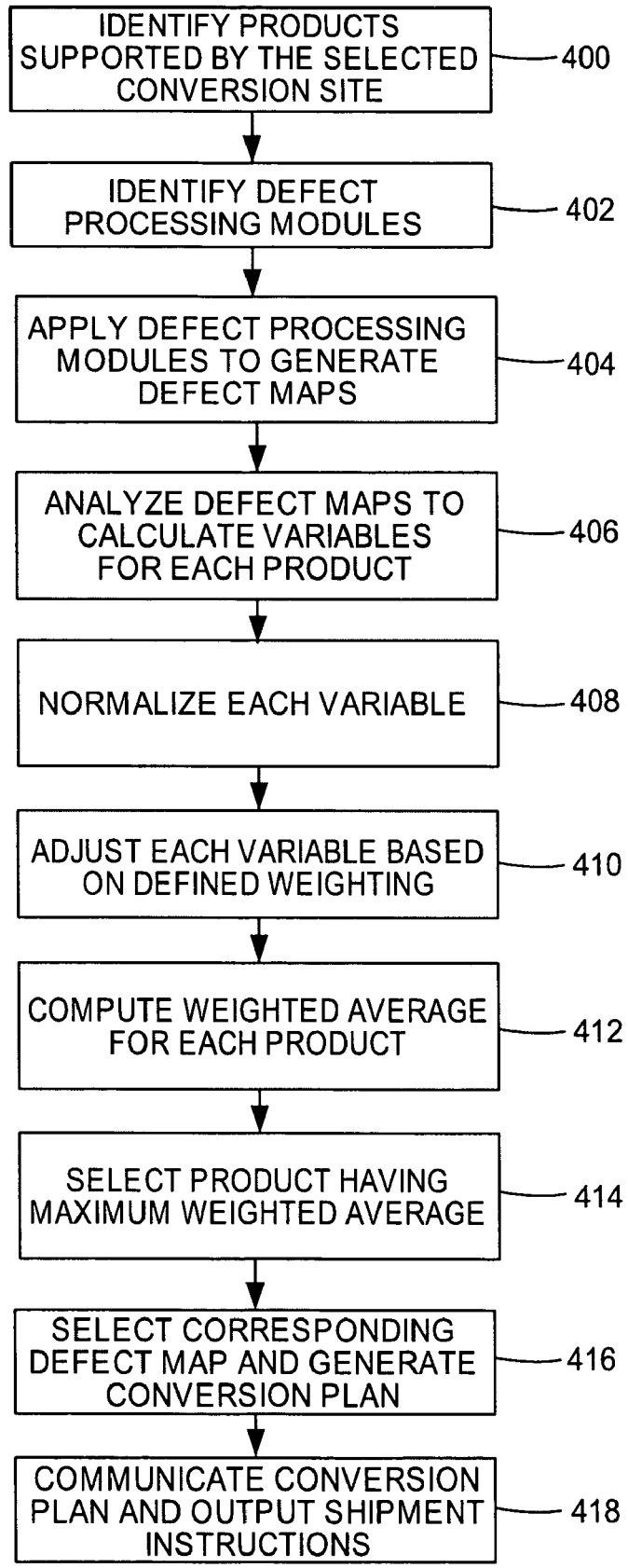
FIG. 15 is a flowchart illustrating an exemplary method in which the conversion control engine generates a conversion plan for a given web roll based on a weighted average of a plurality of configurable parameters.

FIG. 15 is a flowchart illustrating an exemplary method in which conversion control engine 64 generates a conversion plan 72I for a given web roll 10 based on a weighted average of a plurality of configurable parameters. Conversion control engine 64 identifies a set of potential products 12 into which the web roll 10 may be converted, and selectively invokes one or more of the defect processing modules 60 to apply defect detection algorithms and generates defect maps 72F for the web roll (400–404).

Next, conversion control engine 64 employs any of the described techniques to calculate the specified parameters, e.g., web utilization, component yield, profit, sales, process capacity, process time or other parameters for each of the products (406). Conversion control engine 64 then normalizes each of the parameters to a common range, such as 0 to 100 (408).

Conversion control engine 64 then adjusts each of the parameters in accordance with a user-configurable weighting, as shown in FIG. 6 (410), and computes a total weighted average for each product (412). Conversion control engine 64 selects the product corresponding to the maximum weighted average of the parameters (414), generates a conversion plan 72I for the selected product based on the respective defect map (416).

Conversion control engine 64 communicates the conversion plan to the appropriate converting site 8, and outputs (e.g., display or print) shipment instructions for shipping the particular web roll 10 to the converting site (418). In this manner, conversion control engine 64 may consider multiple parameters when defining a conversion plan 72I for converting the web roll into products based on stored image anomaly information.

Figure 16:
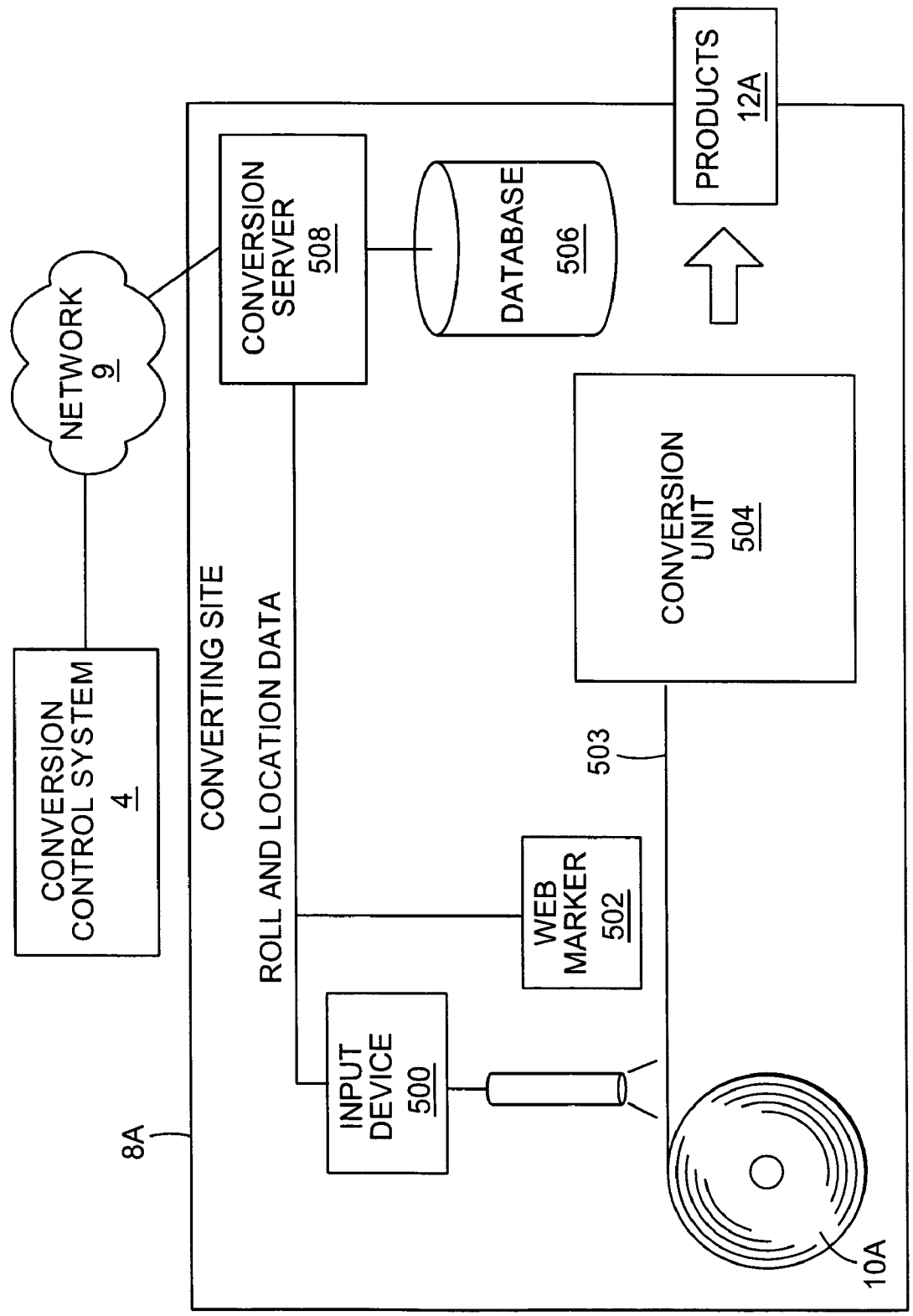
FIG. 16 is a block diagram illustrating one embodiment of a converting site.

FIG. 16 is a block diagram illustrating one embodiment of a converting site 8A. In this exemplary embodiment, converting site 8A includes a web roll 10A that has been loaded and readied for conversion.

Conversion server 508 receives conversion maps from conversion control system 4, and stores the conversion maps in database 506. A barcode is read from roll 10A, which informs conversion server 508 of the particular web 503, allowing the conversion server to access database 506 and retrieve the corresponding conversion map. The barcode may be read by input device 500 when web 503 is placed in motion or via a hand-held barcode device prior to loading.

Conversion server 508 displays a conversion plan, thereby allowing workers to configure conversion unit 504. Specifically, conversion unit 504 is configured to physically cut web 503 into numerous individual sheets (i.e., products 12A) in accordance with the conversion plan.

As web 503 passes through the system during the marking operation, input device 500 reads barcodes and associated fiducial marks are regularly sensed. The combination of barcode and fiducial mark enables one to precisely register the physical position of web 503 to the defects identified in the conversion plan. Regular re-registration ensures ongoing registration accuracy. One skilled in the art is capable of establishing the re-registration through conventional physical coordinate transformation techniques. Once web 503 is registered to the conversion map, the physical position of specific defects is known.

When defects pass under web marker 502, marks are applied to web 503 to visually identify the defects. Specifically, conversion server 508 outputs a series of commands to a web marker 502, which then applies locating marks to the web 503. In many applications of the present invention, web marker 502 places the locating marks on or adjacent to the defects within web 503 in accordance with the respective conversion plan. However, in some specialized applications the locating marks are spaced in a predetermined way from the anomalies whose position they identify. Web marker 502 may include, for example, a series of ink-jet modules, each having a series of jet nozzles.

The type of mark and the exact position of the mark on or near the defect may be selected based upon the web material, defect classification, web processing required to address the defect, and the intended end use application of the web. In the case of the arrayed ink marker, markers are fired preferentially depending on their cross-web position as defects pass the unit in the down-web direction. With this method, marking accuracies of less than 1 mm have been regularly achieved on high-speed webs with production rates greater than 150 ft/minute. However, higher speed webs in excess of 1000 meter/minute are within the capability of the invention.

Conversion server 508 may pause the conversion of web 503 at any point in accordance with the conversion plan to allow reconfiguration of conversion unit 504. For example, in the even web 503 is to be converted to different products, conversion server 508 halts the conversion process after the first product is produced to allow conversion unit 504 to be reconfigured for the subsequent product. Positioning of cutting devices and other mechanisms, for example, may be reconfigured as needed to produce the second product.

Figure 17:
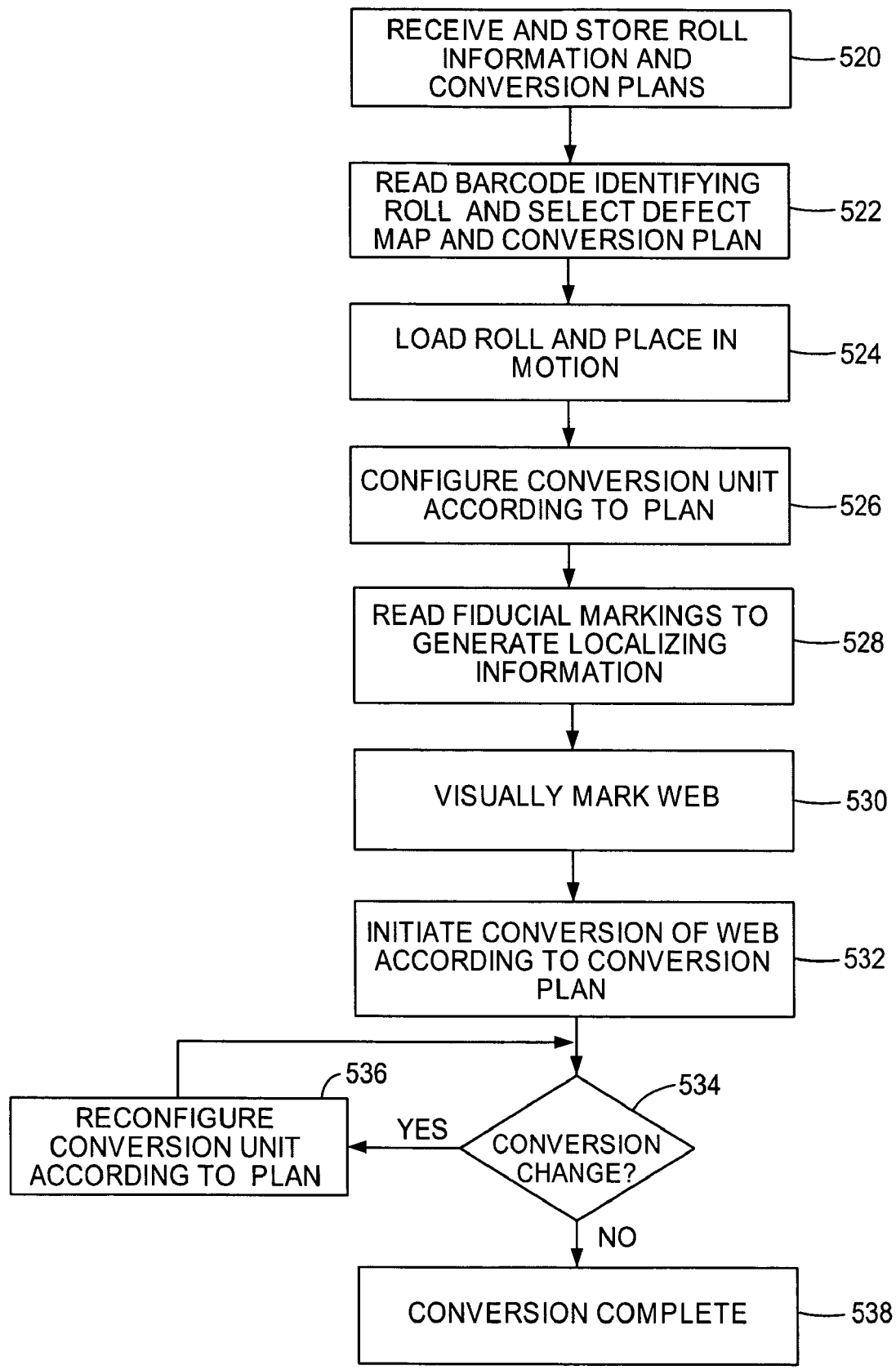
FIG. 17 is a flowchart illustrating exemplary operation of the converting site in processing a web in accordance with a conversion plan to achieve a maximum yield or other configurable parameter.

FIG. 17 is a flowchart illustrating exemplary operation of a converting site, such as converting site 8A of FIG. 16, in processing a web in accordance with conversion plans to achieve, for example, a maximum yield or other configurable parameter.

Initially, conversion server 508 receives and stores roll information and conversion plans from conversion control system 4 (520). This may happen prior to or after receiving web rolls. For example, conversion server 508 may receive roll information and a conversion plan for a particular web roll weeks before the physical web roll arrives at the converting sites. Alternatively, conversion server 508 may receive roll information and a conversion plan for a web roll already stored within inventory at the converting site.

Next, conversion server 508 receives barcode information, for a particular web roll to be converted, causing conversion server 508 to access database 506 and retrieve the corresponding conversion map (522). As noted above, the barcode may be read prior to loading (e.g., by a hand-held barcode device), as illustrated in FIG. 17, or via input device 500 after web 503 is loaded and readied for conversion.

Conversion server 508 displays a conversion plan, thereby allowing workers to configure conversion unit 504 to physically cut web 503 into numerous individual sheets (i.e., products 12A) in accordance with the conversion plan (526). Alternatively, conversion unit 504 may be configured in an automated or semi-automated manner in accordance with the conversion plan.

Once conversion unit 504 is configured, web 503 is set in motion and input device 500 reads barcodes and senses associated fiducial marks (528), and web marker 502 may be utilized to visually mark web 503 in order to assist in the visual recognition of defective products (530). Conversion unit 504 converts the received web 503 to form products 12A (532).

At any point within the conversion plan, conversion server 508 may determine that a reconfiguration is required by the plan (534). If so, conversion server 508 directs the reconfiguration of conversion unit 504 (536). This process continues until all of web 503 is converted to one or more products 12A in accordance with the conversion plan (538).

Various embodiments of the invention have been described. These and other embodiments are within the scope of the following claims.

What is claimed is:

1. A method comprising:
   imaging a sequential portion of a web to provide digital information;
   processing the digital information with at least one initial algorithm to identify regions on the web containing anomalies;
   analyzing at least a portion of the digital information with a plurality of subsequent algorithms to determine which anomalies represent actual defects in the web for a plurality of different products;
   determining a value of at least one product selection parameter for each of the products;
   selecting at least one of the products based on the determined value for each of the products; and
   converting the web into the selected product or products.

2. The method of claim 1, wherein determining a value comprises computing the respective determined value for each of the products based on the determined actual defects for the respective products.

3. The method of claim 1, wherein determining a value comprises computing a web utilization for each of the products based on the determined actual defects for the respective products.

4. The method of claim 1, wherein determining a value comprises:
  computing an estimated number of components that would be produced for each of the products based on the determined actual defects for the respective products; and
  computing an estimated total sales for each of the products based on the computed number of components.

5. The method of claim 1,
  wherein determining a value comprises determining a process time for conversion of the web for the respective products, and
  wherein selecting one of the products comprises selecting the product to minimize the process time for the web.

6. The method of claim 1,
  wherein determining a value comprises determining a machine utilization for one or more converting sites, and
  wherein selecting one of the products comprises selecting the product based on the determined machine utilization.

7. The method of claim 1, further comprising:
  determining a value for a first product selection parameter for each of the products;
  determining a value for a second product selection parameter for each of the products; and
  selecting the product based on the determined first and second values for each of the products.

8. The method of claim 1, wherein determining a value comprises determining values for a plurality of product selection parameters, the method further comprising:
  computing a weighted average of the values for each of the products; and
  selecting the product based on the respective computed weighted averages.

9. The method of claim 1, wherein converting the web comprises:
  generating a conversion plan for the web based on the determined actual defects and the selected product; and
  wherein converting the web into the selected product or products comprises converting the web in accordance with the generated conversion plan.

10. The method of claim 1, wherein the at least one subsequent algorithm characterizes at least a portion of the web into quality classifications.

11. A system comprising:
  an imaging device that images a sequential portion of a web to provide digital information;
  an analysis computer that processes the digital information with an initial algorithm to identify regions on the web containing anomalies; and
  a conversion control system that analyzes at least a portion of the digital information with at least one subsequent algorithm to determine which anomalies represent actual defects in the web for a plurality of different products,
  wherein the conversion control system determines a value of at least one product selection parameter for each of the products, and selects one of the products for conversion of the web based on the determined value for each of the products.

12. The system of claim 11, wherein the conversion control system generates a conversion plan for the web based on the determined actual defects and the selected product.

13. The system of claim 12, further comprising:
  a conversion server located within a converting sites and coupled to the conversion control system by a network,
  wherein the conversion control system electronically communicates the conversion plan to the conversion server located with the converting sites.

14. The system of claim 13, wherein the conversion server displays the conversion plan for converting the web to the selected product.

15. The system of claim 13, wherein the conversion server controls configuration of a process line within the conversion in accordance with the conversion plan.

16. The system of claim 11, wherein the conversion control system computes the respective value for each of the products based on the determined actual defects for the respective products.

17. The system of claim 11, wherein the conversion control system computes one or more of an estimated utilization of the web for each of the products, an estimated number of components that would be produced for each of the products, an estimated total sales for each of the products, a process time for conversion of the web to each of the respective products or a machine utilization for one or more converting sites associates with the products.

18. The system of claim 11, wherein the conversion control system determining values for a plurality of product selection parameters, computes a weighted average of the values for each of the products; and selects the product based on the respective computed weighted averages.

19. The system of claim 11, wherein the analysis computer process the digital information with the initial algorithm and extracts a portion of the digital information for each of the identified regions, and the conversion control system analyzes the extracted portions of the digital information to determine the actual defects for the plurality of different products.

20. The system of claim 11, wherein the conversion control system comprises:
  a user interface module that presents a user interface to display the product selection parameter as one of a plurality of user-selectable product selection parameters;
  a database storing data defining a set of conversion control rules; and
  a conversion control engine that, for each products, applies the conversion control rules to determines values for the product selection parameters selected by a user, and selects the product based on the determined values.

21. A conversion control system comprising:
  a database storing data defining a set of rules;
  an interface to receive anomaly information from an analysis machine, wherein the anomaly information identifies regions of a web containing anomalies; and
  a conversion control engine that applies the rules to the anomaly information to determine a value for at least one product selection parameter for each of a plurality of products,
  wherein the conversion control engine selects one of the products for conversion of the web based on the determined values.

22. The conversion control system of claim 21, further comprising a plurality of defect processing modules that apply image processing algorithms to determine which anomalies represent actual defects in the web for the different products.

23. The conversion control system of claim 21, wherein the database stores product data that defines each of the products into which the web can be converted.

24. The conversion control system of claim 23,
wherein the product data stores data specifying an estimated revenue per unit for each of the products, an estimated income per unit for each of products, an estimated conversion time to convert a web roll to each product, a current level of industry demand for each of product, and
wherein the conversion engine utilizes the product data when applying the rules.

25. A computer-readable medium comprising instructions that cause a processor to:
store data defining a set of rules;
receive anomaly information from an analysis machine located within a manufacturing plant, wherein the anomaly information identify regions of a web containing anomalies;
apply the rules to the anomaly information to determine a value for at least one product selection parameter for each of a plurality of products; and
select one of the products for conversion of the web based on the determined values.

26. The computer-readable medium of claim 25, wherein the instruction cause the processor to compute one or more of an estimated utilization of the web for each of the products, an estimated number of components that would be produced for each of the products, an estimated total sales for each of the products, a process time for conversion of the web to each of the respective products or a machine utilization for one or more converting sites associates with the products.

27. The computer-readable medium of claim 25, wherein the instruction cause the processor to:
generate a conversion plan for the web based on the determined actual defects and the selected product;
communicate the conversion plan to a converting site for controlling conversion of the web; and
output shipment instructions for shipment of the web to the converting site for conversion.

28. A method comprising:
imaging a sequential portion of a web to provide digital information;
processing the digital information with at least one initial algorithm to identify regions on the web containing anomalies;
analyzing at least a portion of the digital information with a plurality of subsequent algorithms to determine which anomalies represent actual defects in the web for a plurality of different products;
selecting non-overlapping regions of the web for at least two of the products;
generating a composite defect map based on the selected non-overlapping regions;
generating a conversion plan based on the composite defect map; and
converting the web in accordance with the conversion plan.

29. A system comprising:
an imaging device that images a sequential portion of a web to provide digital information;
an analysis computer that processes the digital information with an initial algorithm to identify regions on the web containing anomalies; and
a conversion control system that analyzes at least a portion of the digital information with at least one subsequent algorithm to determine which anomalies represent actual defects in the web for a plurality of different products and, based on the analysis, selects non-overlapping regions of the web for at least two of the products, and generates a composite defect map on the selected non-overlapping regions.

30. The method of claim 29, wherein the conversion control system additionally generates a conversion plan based on the composite defect map.

31. The method of claim 30, wherein the conversion control system additionally converts the web in accordance with the conversion plan.

* * * * *

UNITED STATES PATENT AND TRADEMARK OFFICE
CERTIFICATE OF CORRECTION

| | | |
|---|---|---|
| PATENT NO. | : 7,187,995 B2 | Page 1 of 1 |
| APPLICATION NO. | : 11/025242 | |
| DATED | : March 6, 2007 | |
| INVENTOR(S) | : Steven P. Floeder | |

It is certified that error appears in the above-identified patent and that said Letters Patent is hereby corrected as shown below:

On Page 2 of the Title Pages, Col. 2, under (Other Publications)
Line 15, after "Detection" insert -- in --.

Col. 6
Line 26, after "that" delete "10".

Col. 9
Line 49, delete "conversions" and insert -- conversion --, therefor.

Col. 12
Line 54, after "having" insert -- Attorney Docket No. 58695US002, --.

Col. 19
Line 10, in Claim 5, delete "determining a value comprises determining a" and insert -- the product selection parameter is --, therefor.
Line 16, in Claim 6, delete "determining a value comprises determining a" and insert -- the product selection parameter is --, therefor.

Signed and Sealed this

Eighth Day of May, 2007

JON W. DUDAS
*Director of the United States Patent and Trademark Office*